US012564693B2

(12) United States Patent
Alonso Babarro

(10) Patent No.: US 12,564,693 B2
(45) Date of Patent: Mar. 3, 2026

(54) LARYNGEAL MASK AIRWAY INTUBATION GUIDE AND METHOD

(71) Applicant: Airway Medical Innovations Pty Ltd, Queensland (AU)

(72) Inventor: Julio Miguel Alonso Babarro, Fortitude Valley (AU)

(73) Assignee: Airway Medical Innovations Pty Ltd, Fortitude Valley (AU)

( * ) Notice: Subject to any disclaimer, the term of this patent is extended or adjusted under 35 U.S.C. 154(b) by 621 days.

(21) Appl. No.: 18/012,351

(22) PCT Filed: Jun. 24, 2020

(86) PCT No.: PCT/AU2020/050640
§ 371 (c)(1),
(2) Date: Dec. 22, 2022

(87) PCT Pub. No.: WO2020/257852
PCT Pub. Date: Dec. 30, 2020

(65) Prior Publication Data
US 2023/0270963 A1 Aug. 31, 2023

(51) Int. Cl.
*A61M 16/04* (2006.01)

(52) U.S. Cl.
CPC .... *A61M 16/0495* (2014.02); *A61M 16/0434* (2013.01)

(58) Field of Classification Search
None
See application file for complete search history.

(56) References Cited

U.S. PATENT DOCUMENTS

| | | | |
|---|---|---|---|
| 2,756,742 | A | 7/1956 | Barton |
| 3,316,913 | A | 5/1967 | Swenson |

(Continued)

FOREIGN PATENT DOCUMENTS

| | | |
|---|---|---|
| DE | 202012003341 | 8/2012 |
| EP | 1542578 | 6/2005 |

(Continued)

OTHER PUBLICATIONS

AU Office Action in Australian Appln. No. 2019295405, mailed on Feb. 17, 2025, 5 pages.

(Continued)

*Primary Examiner* — LaToya M Louis
(74) *Attorney, Agent, or Firm* — Fish & Richardson P.C.

(57) ABSTRACT

A laryngeal mask airway (LMA) intubation guide for use in an endotracheal intubation procedure and in ventilation of a subject, the LMA intubation guide including: an elongate body defining a passageway extending between a proximal opening and a distal opening, for receiving a blade portion of an intubation device; a laryngeal mask at the distal opening, for covering the larynx of the subject; and a ventilation airway extending at least partially along the body, including: a ventilation port at a proximal end of the ventilation airway for connection to a ventilator; and a ventilation aperture at a distal end of the ventilation airway for allowing fluid communication between the ventilation airway and the passageway proximate to the laryngeal mask, the LMA intubation guide being configured to allow intubation of the subject using an endotracheal tube through the passageway, while the subject is ventilated using the ventilation airway.

27 Claims, 17 Drawing Sheets

(56)     References Cited

U.S. PATENT DOCUMENTS

| | | | |
|---|---|---|---|
| 4,069,820 A | | 1/1978 | Berman |
| 4,240,417 A | * | 12/1980 | Holever ............ A61M 16/0465 |
| | | | 128/207.15 |
| 4,693,243 A | | 9/1987 | Buras |
| 4,848,331 A | * | 7/1989 | Northway-Meyer ........................ |
| | | | A61M 16/0495 |
| | | | 128/207.14 |
| 5,184,603 A | | 2/1993 | Stone |
| 5,197,463 A | | 3/1993 | Jeshuran |
| 5,509,408 A | | 4/1996 | Kurtis |
| 5,643,221 A | | 7/1997 | Bullard |
| 5,694,929 A | * | 12/1997 | Christopher ...... A61M 16/0409 |
| | | | 128/207.14 |
| 5,776,052 A | | 7/1998 | Callahan |
| 5,964,217 A | | 10/1999 | Christopher |
| 6,251,069 B1 | | 6/2001 | Mentzelopoulos et al. |
| 6,568,388 B2 | | 5/2003 | Christopher |
| 6,763,831 B2 | | 7/2004 | Sniadach |
| 7,438,717 B2 | | 10/2008 | Tylke |
| 7,608,040 B1 | | 10/2009 | Dunst |
| 8,382,665 B1 | | 2/2013 | Fam |
| 8,960,195 B2 | | 2/2015 | Lehman |
| 9,327,091 B2 | | 5/2016 | Wang |
| 9,364,631 B2 | | 6/2016 | Tylke |
| 10,531,792 B2 | | 1/2020 | Babarro et al. |
| 12,226,575 B2 | * | 2/2025 | Zayed ................. A61B 1/00142 |
| 2002/0108610 A1 | * | 8/2002 | Christopher ...... A61M 16/0427 |
| | | | 128/207.15 |
| 2003/0047189 A1 | | 3/2003 | Kumar |
| 2003/0195390 A1 | | 10/2003 | Graumann |
| 2004/0079364 A1 | * | 4/2004 | Christopher ...... A61M 16/0409 |
| | | | 128/207.14 |
| 2006/0276694 A1 | | 12/2006 | Acha Gandarias |
| 2009/0032016 A1 | | 2/2009 | Law |
| 2009/0044799 A1 | | 2/2009 | Qui |
| 2009/0211574 A1 | | 8/2009 | Sniadach |
| 2010/0191062 A1 | | 7/2010 | Kieffer |
| 2010/0249513 A1 | | 9/2010 | Tydlaska |
| 2010/0261967 A1 | | 10/2010 | Pacey et al. |
| 2013/0296653 A1 | | 11/2013 | Brown |
| 2013/0310650 A1 | | 11/2013 | Hales |
| 2013/0333232 A1 | | 12/2013 | Kildevaeld |
| 2014/0000622 A1 | | 1/2014 | Azagury |
| 2014/0135787 A1 | | 5/2014 | Tylke |
| 2014/0144432 A1 | | 5/2014 | Avitsian |
| 2014/0173912 A1 | | 6/2014 | Scimone |
| 2014/0332000 A1 | | 11/2014 | Stegman et al. |
| 2014/0336676 A1 | | 11/2014 | Pong |
| 2015/0283344 A1 | | 10/2015 | Olympio |
| 2015/0314094 A1 | | 11/2015 | Avitsian et al. |
| 2015/0336782 A1 | | 11/2015 | Boyajian |
| 2016/0114117 A1 | | 4/2016 | Cook |
| 2017/0325667 A1 | | 11/2017 | Babarro et al. |
| 2018/0104427 A1 | * | 4/2018 | Avitsian ............ A61M 16/0486 |
| 2018/0169365 A1 | * | 6/2018 | Sawyer ............. A61M 16/0434 |
| 2018/0207383 A1 | * | 7/2018 | Gardner ............ A61M 16/0463 |
| 2018/0272090 A1 | | 9/2018 | Blom |
| 2019/0059710 A1 | * | 2/2019 | Molnar ................. A61B 1/2676 |
| 2019/0142262 A1 | | 5/2019 | Inglis |
| 2020/0352429 A1 | | 11/2020 | Babarro et al. |
| 2022/0257889 A1 | | 8/2022 | Babarro |
| 2022/0355052 A1 | | 11/2022 | Babarro |
| 2022/0355053 A1 | | 11/2022 | Babarro |
| 2022/0395170 A1 | | 12/2022 | Babarro et al. |
| 2023/0284930 A1 | * | 9/2023 | Rockwell .......... A61M 16/0493 |

FOREIGN PATENT DOCUMENTS

| | | |
|---|---|---|
| EP | 2679144 | 1/2014 |
| EP | 3150245 | 4/2017 |
| GB | 2332375 | 6/1999 |
| JP | 2012-196300 | 10/2012 |
| JP | 2013-502961 A | 1/2013 |
| JP | 2013-192820 | 9/2013 |
| KR | 20140130355 A | 11/2014 |
| KR | 101508839 | 4/2015 |
| WO | WO 2001/091838 | 12/2001 |
| WO | WO 2003/047673 | 6/2003 |
| WO | WO 2009/026095 | 2/2009 |
| WO | WO 2011/023930 | 3/2011 |
| WO | WO 2011/119521 | 9/2011 |
| WO | WO 2014/078559 A1 | 5/2014 |
| WO | WO 2014/084769 | 6/2014 |
| WO | WO 2016/090435 | 6/2016 |
| WO | WO 2018/109033 | 6/2018 |
| WO | WO 2020/000031 | 1/2020 |

OTHER PUBLICATIONS

AU Office Action in Australian Appln. No. 2019295406, mailed on Dec. 23, 2024, 3 pages.

AU Office Action in Australian Appln. No. 2020302956, mailed on Feb. 27, 2025. 3 pages.

JP Office Action in Japanese Appln. No. 2021-576822, mailed on Jun. 18, 2024, 9 pages (with English translation).

U.S. Office Action in United States U.S. Appl. No. 17/621,544, mailed on Jan. 29, 2025, 33 pages.

U.S. Office Action in United States U.S. Appl. No. 17/621,608, mailed on Aug. 21, 2024, 32 pages.

U.S. Office Action in United States U.S. Appl. No. 17/621,612, mailed on Nov. 22, 2024, 16 pages.

U.S. Restriction Requirement in U.S. Appl. No. 17/621,612, mailed on Apr. 23, 2024, 7 pages.

AU Australian Examination Report No. 1 for AU Appln. No. 2019204961, Sep. 10, 2020, 4 pages.

AU First Examination Report; AU Application No. 2015362090; Feb. 1, 2017; 2 pages.

AU First Examination Report; AU Application No. 2017251785; Apr. 6, 2018; 3 pages.

CN Office Action in Chinese Appln. No. 201580074269.7, dated Feb. 18, 2020, 12 pages (with English Translation).

CN Office Action in Chinese Appln. No. 201580074269.7, dated Jun. 19, 2019, 11 pages (with English Translation).

CN Office Action with English Translation; CN Appln. No. 201580074269.7; Aug. 28, 2018; 17 pages.

EP Extended Search Report in European Appln. No. 19825304.9, dated Jan. 23, 2023, 8 pages.

EP Supplemental European Search Report in European Appln. No. 15867493.7, dated Jun. 29, 2018, 8 pages.

Glide Rite AutoStylet Brochure; Verathon Inc., Jan. 2010; 2 pages.

PCT International Preliminary Report on Patentability in International Appln. No. PCT/AU2015/050786, dated Dec. 21, 2016, 7 pages.

PCT International Preliminary Report on Patentability in International Appln. No. PCT/AU2019/050652, dated Dec. 28, 2021, 8 pages.

PCT International Preliminary Report on Patentability in International Appln. No. PCT/AU2019/050653, dated Dec. 28, 2021, 5 pages.

PCT International Preliminary Report on Patentability in International Appln. No. PCT/AU2019/050659, dated Dec. 28, 2021, 9 pages.

PCT International Preliminary Report on Patentability in International Appln. No. PCT/AU2020/050639, dated Dec. 28, 2021, 10 pages.

PCT International Preliminary Report on Patentability in International Appln. No. PCT/AU2020/050640, dated Aug. 24, 2020, 9 pages.

PCT International Search Report and Written Opinion in International Appln. No. PCT/AU2015/050786; Feb. 17, 2016.

PCT International Search Report and Written Opinion in International Appln. No. PCT/AU2019/050652, dated Jul. 26, 2019, 17 pages.

PCT International Search Report and Written Opinion in International Appln. No. PCT/AU2019/050653, dated Sep. 16, 2019, 8 pages.

(56) References Cited

OTHER PUBLICATIONS

PCT International Search Report and Written Opinion in International Appln. No. PCT/AU2019/050659, dated Jan. 2, 2020, 14 pages.
PCT International Search Report and Written Opinion in International Appln. No. PCT/AU2020/050639, dated Aug. 10, 2020, 14 pages.
PCT International Search Report and Written Opinion in International Appln. No. PCT/AU2020/050640, dated Dec. 13, 2022, 4 pages.

* cited by examiner

LARYNGEAL MASK AIRWAY INTUBATION GUIDE AND METHOD

CROSS-REFERENCE TO RELATED APPLICATIONS

This application is a § 371 National Stage Application of U.S. Patent Application Ser. No. PCT/AU2020/050640, filed on Jun. 24, 2020 the entire contents of which are hereby incorporated by reference.

BACKGROUND OF THE INVENTION

The present invention relates to a laryngeal mask airway intubation guide and a method for use in an endotracheal intubation procedure, being particularly adapted to allow ventilation of a subject using a laryngeal mask airway throughout the procedure.

DESCRIPTION OF THE PRIOR ART

Endotracheal intubation is the procedure through which a medical professional introduces a flexible plastic conduit, an endotracheal tube, generally through the mouth and into the trachea. This allows artificial ventilation, which is required when the breathing ability is compromised by an illness or injury in an emergency situation or is interfered by drug-induced depression during surgery. It is a universal procedure and is performed in the same fashion all over the world.

Every day thousands of intubations are performed by a diverse range of professionals, particularly anaesthetics specialists, intensivists, emergency physicians and pre-hospital medics and paramedics. However endotracheal intubation is a high risk procedure which can lead to death or disability, requires considerable skill and occasionally cannot be accomplished. Even to highly trained professionals, it is often difficult and sometimes unsuccessful. New specialised instruments and advanced techniques are continuously developing with the aim to facilitate this difficult procedure and ensure better success rates.

The aim of the operator is to successfully pass an endotracheal tube through the mouth, pharynx and larynx and into the trachea. The oropharyngeal passage is curved and narrow and ends at the entrance of both the larynx and the oesophagus. The tongue tends to fall back on to the pharynx when a patient is in supine position, the entrance of the larynx can vary in its position due to the particular anatomy of a patient and the epiglottis lies over the entrance of the larynx and usually needs to be moved to expose the glottic opening.

The operator needs to identify the vocal cords at the entrance of the larynx, the epiglottis above the entrance of the larynx in the transversal view with the patient supine, and the oesophagus, below all previous structures on this view. This procedure requires extraordinary skills; it is easier for the endotracheal tube to follow the path towards the oesophagus, it is often difficult to obtain a good view of the larynx, and even with a good view, it is difficult sometimes to introduce the endotracheal tube. Any delay in successfully finalising the procedure is a serious complication, and may potentially be fatal.

The insertion of an endotracheal tube through all these anatomical structures and into the trachea is referred to as endotracheal intubation and typically requires the use of an instrument called a laryngoscope which comprises a handle, and a blade. Different shapes of the blade may be used depending on a range of factors such as the age or size of the patient and different procedural options. Laryngoscope blades are generally classified as curved or straight, although a number of styles of curved and straight blades are commercially available. Some styles of blades are designed to be positioned anterior to the epiglottis, and other styles are designed to be positioned posterior to the epiglottis, leading to slightly different movements during the procedure.

During endotracheal intubation, generally with the patient laying supine, the operator, standing at the top of the head of the patient, introduces the blade of the laryngoscope through the mouth and into the pharynx and manipulates anatomical structures such as the tongue and the epiglottis (depending on the particular patient and type of blade) to expose the entrance of the larynx. Then, under direct visualisation, the operator inserts the tip of the endotracheal tube into the larynx and advances it into the trachea. In the conventional and universal procedure, the operator typically utilises the left hand to hold the laryngoscope by the handle to position the blade and utilises the right hand to carefully introduce the endotracheal tube, pushing it alongside the laryngoscope blade and into the visualised trachea.

Often, because of anatomical variations and challenges, and despite an adequate technique, direct visualisation is difficult. In most of these occasions, adequate visualisation could be obtained by manipulating some of the anatomical structures. Unfortunately, with the conventional laryngoscope and conventional procedure, the operator is utilising both hands and the hand being used to manually introduce the endotracheal tube cannot be used to manipulate anatomical structures to facilitate the procedure. Furthermore, a second operator could not have direct visual access to the entrance of the larynx to help manipulating these structures and will interfere with the vision of the first operator, as the mouth opening, through which the first operator is obtaining the view, is very limited and the operator performing the intubation procedure will usually be in the best viewing position. Video laryngoscopes are available to remove the need for a direct view, although these are typically bulkier than conventional laryngoscopes and still occupy both hands of the operator.

Due to the degree of difficulty of the procedure itself, together with the seriousness of the potential complications, this procedure will only be performed by highly skilled professionals. This difficulty and serious complication risk have also meant that the procedure, and the instruments used to perform it, has essentially remained unchanged for decades. The physicians and other professionals who perform endotracheal intubations are unwilling to use new devices or to change the way this is conventionally done, given the difficulties and risks. A new intubation device therefore not only has to offer obvious procedural advantages in comparison to the conventional laryngoscopes, but also has to present similar characteristics in shape and weight and in its method of use, to facilitate adoption by operators already trained and comfortable in the use of conventional laryngoscopes in the often stressful circumstances of performing an intubation procedure.

WO/2016/090435A1 discloses a new intubation device that allows an endotracheal intubation procedure to be performed using a single hand. In particular, the intubation device includes: a laryngoscope blade having a tip and a base; a handle attached to the base of the blade for allowing the intubation device to be held in a hand of a user; a channel for receiving an endotracheal tube, the channel including a blade channel portion extending along the blade substantially from the tip to the base and including an outlet proximate to the tip for allowing a distal end of the endotracheal tube to be advanced from the outlet and a handle channel portion extending partially along the handle from the blade channel portion; and a tube movement mechanism in the handle for moving the endotracheal tube through the channel to thereby advance the endotracheal tube, the tube movement mechanism including a thumb interface for allowing the user to operate the tube movement mechanism using a thumb of the hand that is holding the intubation device, to thereby allow the user to hold the intubation device and advance the endotracheal tube in an endotracheal intubation procedure using a single hand. The entire contents of WO/2016/090435A1 are incorporated herein by reference.

By enabling single handed operation of the intubation device for positioning the blade via the handle and advancing the endotracheal tube, the other hand of the user will remain free for other uses, such as clearing the airway using another device, such as a suction device, or other devices such as forceps or the like to manipulate anatomical structures and/or the endotracheal tube, during the endotracheal intubation procedure as may be required.

Whilst such a single handed intubation device can help to significantly reduce the difficulty and serious complication risk of endotracheal intubation procedure, one remaining problem is that there will be a period of time during the procedure in which artificial ventilation cannot be provided to the patient. Typically, a patient will be ventilated by mask prior to the procedure until a sufficiently high blood oxygen saturation level is achieved. Typically this may involve pre-oxygenation to reach a 100% blood oxygen saturation, and optionally sedation or paralysis of the patient. When the desired blood oxygen saturation level is achieved, ventilation is discontinued and the mask is removed to expose the patient's mouth and allow the endotracheal intubation procedure to be performed. During the procedure, the patient will not be ventilated and it is therefore vital that the endotracheal intubation is completed as quickly as possible so that ventilation can be resumed via the endotracheal tube. If complications arise during the intubation procedure, there can be a significant risk associated with interrupting ventilation for an excessive period of time. This risk can be exacerbated in situations where the patient is severely ill or injured before the intubation procedure, making ventilation even more critical. It would be therefore be desirable to provide a method and apparatus for allowing an endotracheal intubation procedure to be performed without interrupting ventilation.

U.S. Pat. No. 5,964,217A discloses a method and apparatus for ventilation/oxygenation during guided insertion of an endotracheal tube. An endotracheal tube can be inserted into a patient's trachea during resuscitation by using a face mask and a curved guide. The guide is inserted through a flexible port in the face mask and has a curved distal portion that extends into the patient's mouth and hypopharynx. The patient is initially resuscitated by supplying a flow of air/oxygen through the mask. An endotracheal tube is inserted over the distal end of a fiber optic probe. Resuscitation, oxygenation, or artificial ventilation continue without interruption while the fiber optic probe and endotracheal tube are inserted through a flexible port at the proximal end of the curve guide and then advanced along the guide into the patient's airway. The direction of the distal tip of the fiber optic probe can be controlled by the physician. This allows the physician to carefully guide the fiber optic probe and endotracheal tube to a position past the larynx while resuscitation continues. The fiber optic probe is then removed from within the endotracheal tube and the mask is removed while leaving the endotracheal tube in place within the trachea. The cuff on the endotracheal tube is inflated and a ventilator is connected to the proximal end of the endotracheal tube to ventilate the patient. Alternatively, the patient can be manually ventilated by connecting a resuscitation bag to the proximal end of the endotracheal tube.

However, such an apparatus will only be useful in relatively straightforward intubations which would not require a laryngoscope or intubation device as discussed above. There is a need for an improved method and apparatus to allow ventilated intubation to be performed under a wider range of conditions more likely to be encountered in practice, ideally using an intubation device similar to those already routinely used by medical practitioners.

A laryngeal mask airway (LMA) is a medical device that can be used to provide a ventilation airway during anaesthesia or unconsciousness. The traditional LMA design includes a laryngeal mask that is connected to an airway tube. The laryngeal mask and connected airway tube are inserted through a subject's mouth and pharynx, with the laryngeal mask being positioned over the subject's larynx. The laryngeal mask has a cuff that will form an airtight seal over the larynx, to thereby provide a ventilation airway directly to the larynx. The cuff may be inflatable to allow the laryngeal mask to conform to the subject's anatomy.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE PRESENT INVENTION

In one broad form, an aspect of the present invention seeks to provide a laryngeal mask airway (LMA) intubation guide for use in an endotracheal intubation procedure and in ventilation of a subject, the LMA intubation guide including: an elongate body defining a passageway extending between a proximal opening and a distal opening, the passageway being configured for receiving a blade portion of an intubation device; a laryngeal mask at the distal opening, the laryngeal mask being for covering the larynx of the subject; and a ventilation airway extending at least partially along the body, the ventilation airway including: a ventilation port at a proximal end of the ventilation airway for connection to a ventilator; and a ventilation aperture at a distal end of the ventilation airway for allowing fluid communication between the ventilation airway and the passageway proximate to the laryngeal mask, wherein the LMA intubation guide is configured for insertion into a mouth of the subject so that the proximal opening is positioned proximate to the mouth of the subject and the laryngeal mask is positioned proximate to a larynx of the subject, to thereby allow the blade portion of the intubation device to be inserted into the passageway of the LMA intubation guide to allow intubation of the subject using an endotracheal tube through the passageway, while the subject is ventilated using the ventilation airway.

In one embodiment, the laryngeal mask includes a mask cuff for forming a seal around the larynx of the subject.

In one embodiment, the mask cuff is inflatable.

In one embodiment, the ventilation aperture is located inside the passageway, proximate to the laryngeal mask.

In one embodiment, the ventilation aperture is configured to direct a flow of ventilation gas towards the larynx of the subject.

In one embodiment, the ventilation airway is offset from the passageway.

In one embodiment, the ventilation airway is offset laterally relative to a central plane of the LMA intubation guide that is aligned with a sagittal plane of the subject when the laryngeal mask covers the larynx of the subject.

In one embodiment, the ventilation airway includes an airway body portion that extends along the body.

In one embodiment, at least the airway body portion is formed integrally with the body.

In one embodiment, the ventilation airway includes an airway conduit portion that extends away from the proximal opening.

In one embodiment, the LMA intubation guide includes a closure for covering the proximal opening when the blade portion is not inserted through the passageway.

In one embodiment, the LMA intubation guide includes a seal covering the proximal opening, the seal normally being in a closed position for sealing the proximal opening and being moveable to an open position when the blade portion of the intubation device is inserted through the passageway.

In one embodiment, the seal includes at least one resilient membrane configured to deform in response to the blade portion being urged against the seal, to thereby define an opening for receiving the blade portion.

In one embodiment, the seal includes a resilient membrane that is supported around a perimeter of the proximal opening, the resilient membrane including an aperture that is substantially closed in the closed position and that stretches to define the opening in the open position.

In one embodiment, the aperture is a slit.

In one embodiment, the seal includes two or more resilient membranes that are supported around the perimeter of the proximal opening, the respective aperture of each resilient membrane differing from the apertures of other resilient membranes in at least one of: shape; location; and orientation.

In one embodiment, the seal includes two or more resilient membranes that are each supported around a respective part of a perimeter of the proximal opening and that each include a respective unsupported edge, the unsupported edges at least partially overlapping in the closed position and separating to define the opening in the open position.

In one embodiment, the seal is biased towards the closed position, such that the seal returns towards the closed position when the blade portion of the intubation device is removed from the passageway.

In one embodiment, the seal is configured to form a partial seal surrounding at least one of the blade portion of the intubation device and the endotracheal tube in use.

In one embodiment, the LMA intubation guide includes a removable cap for closing the proximal opening when the blade portion of the intubation device is not being inserted into the passageway of the LMA intubation guide.

In one embodiment, the cap includes a seal for covering the proximal opening, the seal normally being in a closed position for sealing the proximal opening and being moveable to an open position when the blade portion of the intubation device is inserted through the passageway.

In one embodiment, the LMA intubation guide includes a flange surrounding the proximal opening.

In one embodiment, the flange is configured to prevent over-insertion of the LMA intubation guide by abutting the subject's mouth to thereby ensure that the proximal opening remains positioned outside the mouth.

In one embodiment, the LMA intubation guide is configured to be broken along the passageway and the laryngeal mask.

In one embodiment, the body of the LMA intubation guide includes a break line extending longitudinally along a side of the passageway and the laryngeal mask, to thereby allow the LMA intubation guide to be broken along the break line.

In one embodiment, the break line is defined along a central plane of the LMA intubation guide.

In one embodiment, a shape of the proximal opening is selected based on a cross section shape of the blade portion of the intubation device.

In one embodiment, a size of the proximal opening is selected based on a cross section size of the blade portion of the intubation device.

In one embodiment, a shape of the passageway is selected based on a cross section shape of the blade portion of the intubation device.

In one embodiment, a size of the passageway is selected based on a cross section size of the blade portion of the intubation device.

In one embodiment, the LMA intubation guide is formed from a flexible material.

In one embodiment, the LMA intubation guide is configured to expand when receiving the blade portion.

In one embodiment, the LMA intubation guide is curved.

In one embodiment, a curvature of the LMA intubation guide is selected based on a curvature of the blade portion of the intubation device.

In one embodiment, the LMA intubation guide includes a gastric tube conduit for allowing a gastric tube to be advanced into the oesophagus of the subject via the gastric tube conduit.

In one embodiment, the gastric tube conduit extends along the body and includes a gastric tube conduit port at a proximal end of the gastric tube conduit and a gastric tube aperture at a distal end of the gastric tube conduit for allowing the gastric tube to be advanced from the gastric tube aperture into the oesophagus.

In one embodiment, the gastric tube aperture is positioned outside of the laryngeal mask and the passageway.

In one embodiment, the gastric tube aperture is configured to face towards an oesophagus of the subject in use.

In one embodiment, the gastric tube conduit is offset from the passageway.

In one embodiment, the ventilation airway and the gastric tube conduit are offset from the passageway on opposing sides of the passageway.

In one embodiment, the LMA intubation guide is configured to allow the gastric tube to be inserted independently of intubation of the subject being performed.

In one embodiment, the LMA intubation guide is configured to, in use, at least one of: hold a tongue of the subject; and depress the tongue.

In one embodiment, the LMA intubation guide is configured to allow ventilation of the subject independently of intubation of the subject being performed.

In one broad form, an aspect of the present invention seeks to provide a method for use in an endotracheal intubation procedure, the method including: inserting a laryngeal mask airway (LMA) intubation guide into a mouth of a subject, the LMA intubation guide including: an elongate body defining a passageway extending between a proximal opening and a distal opening, the passageway being configured for receiving a blade portion of an intubation device, the proximal opening being positioned proximate to a mouth of the subject; a laryngeal mask positioned at the distal opening and being positioned proximate to a larynx of the subject; and a ventilation airway extending at least partially along the body, the ventilation airway including: a ventilation port at a proximal end of the ventilation airway for connection to a ventilator; and a ventilation aperture at a distal end of the ventilation airway for allowing fluid communication between the ventilation airway and the passageway proximate to the laryngeal mask; covering the larynx of the subject with the laryngeal mask; connecting a ventilator to the ventilation port and ventilating the subject using the ventilation airway; and while ventilation of the subject continues: inserting the blade portion of the intubation device into the passageway of the LMA intubation guide; positioning a distal end of the blade portion of the intubation device proximate to the larynx of the subject; and advancing an endotracheal tube along the blade portion of the intubation device through the passageway into a trachea of the subject.

In one embodiment, the laryngeal mask includes an inflatable mask cuff, the method including inflating the mask cuff after covering the larynx of the subject with the laryngeal mask.

In one embodiment, the method includes, after advancing the endotracheal tube into the trachea of the subject, and while leaving the endotracheal tube in place in the trachea of the subject: withdrawing the blade portion of the intubation device from the LMA intubation guide; and removing the LMA intubation guide from the mouth of the subject.

In one embodiment, the method includes ventilating the subject using the endotracheal tube after advancing the endotracheal tube into the trachea of the subject and before removing the LMA intubation guide.

In one embodiment, the LMA intubation guide is configured to be broken along the passageway and the laryngeal mask, the method including breaking the LMA intubation guide to allow the LMA intubation guide to be removed while the endotracheal tube remains in place.

In one embodiment, the LMA intubation guide includes a closure for covering the proximal opening, the method including removing the closure prior to inserting the blade portion through the passageway.

In one embodiment, the LMA intubation guide includes a seal covering the proximal opening, the seal normally being in a closed position for sealing the proximal opening and being moveable to an open position when the blade portion of the intubation device is inserted through the passageway, the method including inserting the blade portion through the seal of the proximal opening.

In one embodiment, the seal is biased towards the closed position, such that the seal returns towards the closed position when the blade portion of the intubation device is removed from the passageway, the seal forming a partial seal surrounding at least one of the blade portion of the intubation device and the endotracheal tube after inserting the blade.

In one embodiment, ventilating the subject using the ventilation airway includes oxygenating the subject using the ventilation airway.

In one embodiment, the LMA intubation guide includes a gastric tube conduit, the method further including advancing a gastric tube into the oesophagus of the subject via the gastric tube conduit.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

Various examples and embodiments of the present invention will now be described with reference to the accompanying drawings, in which.

DETAILED DESCRIPTION OF THE PREFERRED EMBODIMENTS

An example of a laryngeal mask airway (LMA) intubation guide 110 and a corresponding method for its use in a ventilated endotracheal intubation procedure will now be described with reference to FIGS. 1A to 1J. The laryngeal mask airway (LMA) intubation guide 110 is particularly adapted to allow intubation to be performed using a bladed intubation device 140 (as shown in FIGS. 1D to 1F), such as a laryngoscope or the like. For the purpose of the following examples, it is assumed that the intubation device 140 is a single handed intubation device as described in WO/2016/090435A1, although it should be appreciated that other forms of intubation devices may be used with appropriate adaptations to the apparatus. For example, embodiments of the LMA intubation guide 110 may be configured for use with commercially available video laryngoscopes or conventional, direct vision laryngoscopes.

Figure 1A:
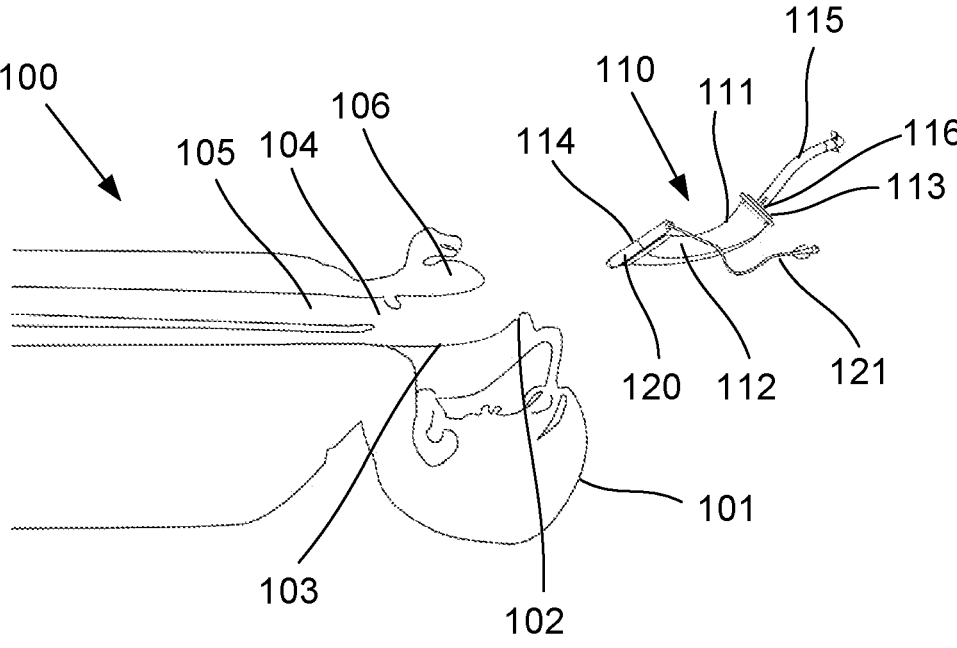
FIGS. 1A to 1J are cross section views showing steps of a ventilated endotracheal intubation procedure being performed on a subject using a first example of a laryngeal mask airway (LMA) intubation guide.

With reference to FIG. 1A, the method commences with the subject 100 lying in a supine position, in a similar manner as per a conventional endotracheal intubation procedure. The subject's head 101 may be tilted, to adjust the relative positioning of the subject's mouth 102, pharynx 103 and larynx 104 to better facilitate access to the larynx during the procedure.

At FIG. 1A, the LMA intubation guide 110 is provided for insertion into the mouth 102 of the subject 100. Further details of the LMA intubation guide 110 can be seen in FIGS. 2A to 2F and FIGS. 3A and 3B.

The LMA intubation guide 110 includes an elongate body 111 defining a passageway 112 extending between a proximal opening 113 and a distal opening 114. The passageway 112 of the LMA intubation guide 110 is configured for receiving a blade portion 142 of an intubation device 140, as shown in FIGS. 1E and 1F, and in further detail in FIGS. 4A and 4B.

The LMA intubation guide 110 also includes a laryngeal mask 120 positioned at the distal opening 114. The laryngeal mask 120 is for covering the larynx of the subject and may have a configuration similar to that of laryngeal masks of traditional laryngeal mask airway devices.

The LMA intubation guide 110 further includes a ventilation airway 115 extending at least partially along the body 111. With regard to FIGS. 2A to 2D, and especially FIGS. 2B and 2D, the ventilation airway 115 includes a ventilation port 211 at a proximal end of the ventilation airway 115 for connection to a ventilator 130 (as shown in FIGS. 1C to 1J) and a ventilation aperture 212 at a distal end of the ventilation airway 115 for allowing fluid communication between the ventilation airway 115 and the passageway 112 proximate to the laryngeal mask 120.

Figure 1B:
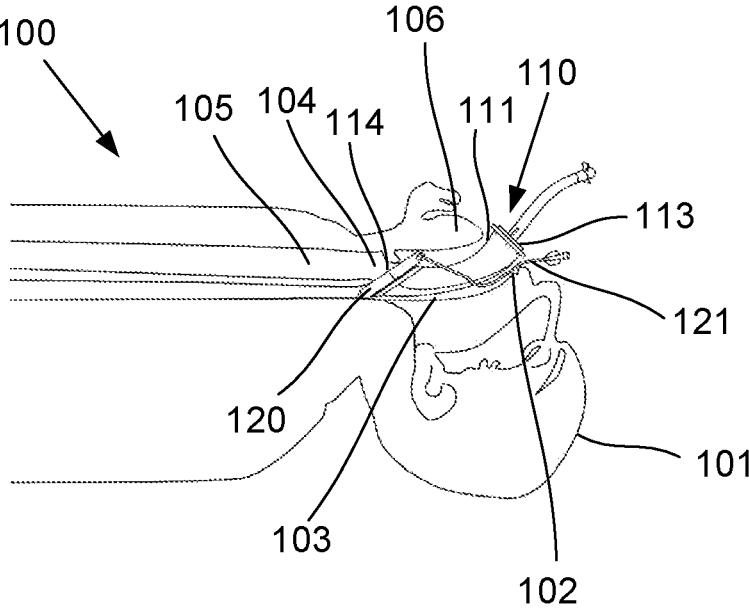

The LMA intubation guide 110 is then inserted into the mouth 102 of the subject 100 as shown in FIG. 1B. When the LMA intubation guide 110 has been properly inserted, the laryngeal mask 120 will be positioned proximate to a larynx 104 of the subject 100 and the proximal opening 113 will be positioned proximate to the mouth 102 of the subject 100. The larynx 104 of the subject 100 will be covered with the laryngeal mask 120.

Further details of the laryngeal mask 120 can be seen in FIGS. 2A to 2D. In this example, the laryngeal mask 120 has a mask cuff 223, which is configured to provide a seal surrounding the larynx 104 of the subject 100. In some examples, the mask cuff 223 may be of an inflatable type, where an inflation gas such as air may be supplied into the mask cuff 223 via an inflation conduit 121. The inflation gas may be supplied via a syringe or other inflation gas source in a similar manner as for inflatable laryngeal masks of traditional laryngeal mask airway devices. The use of an inflatable mask cuff 223 is preferable as this can assist in providing a seal that conforms to the subject's anatomy, but is not essential.

Figure 1C:
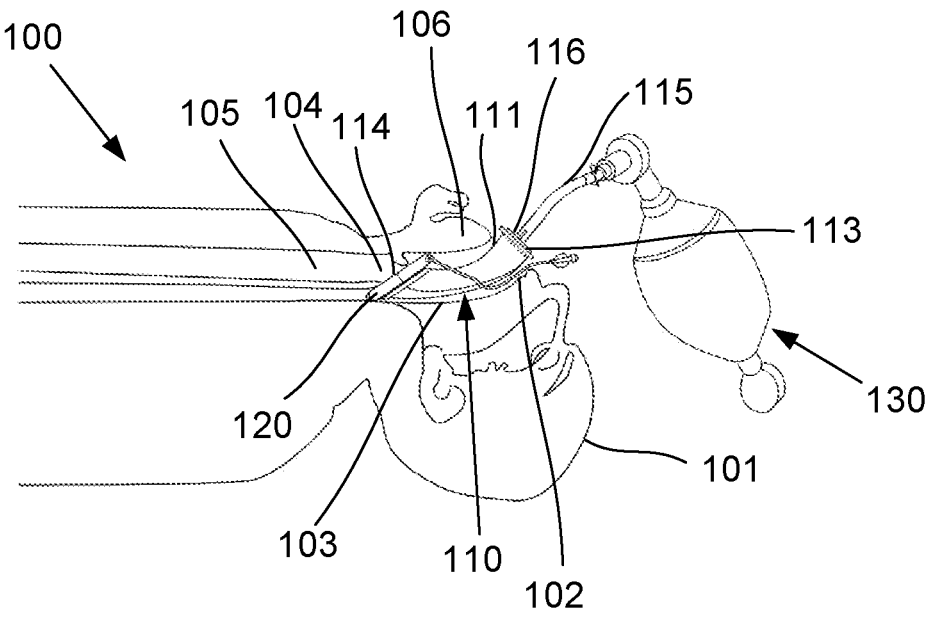
Figure 1D:
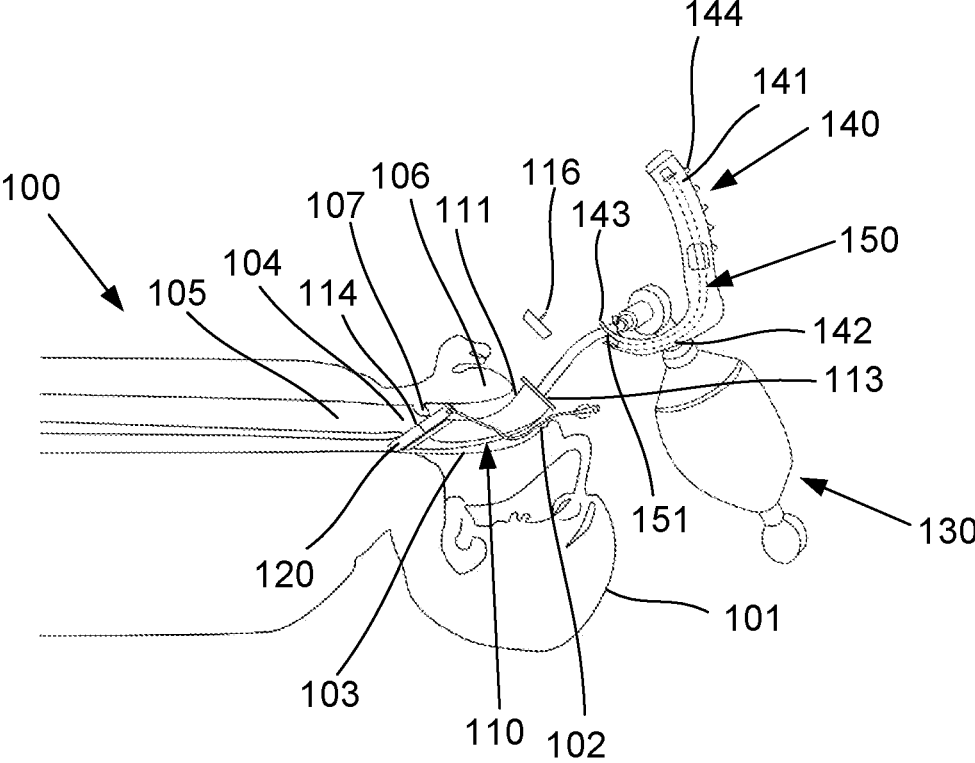
Figure 1E:
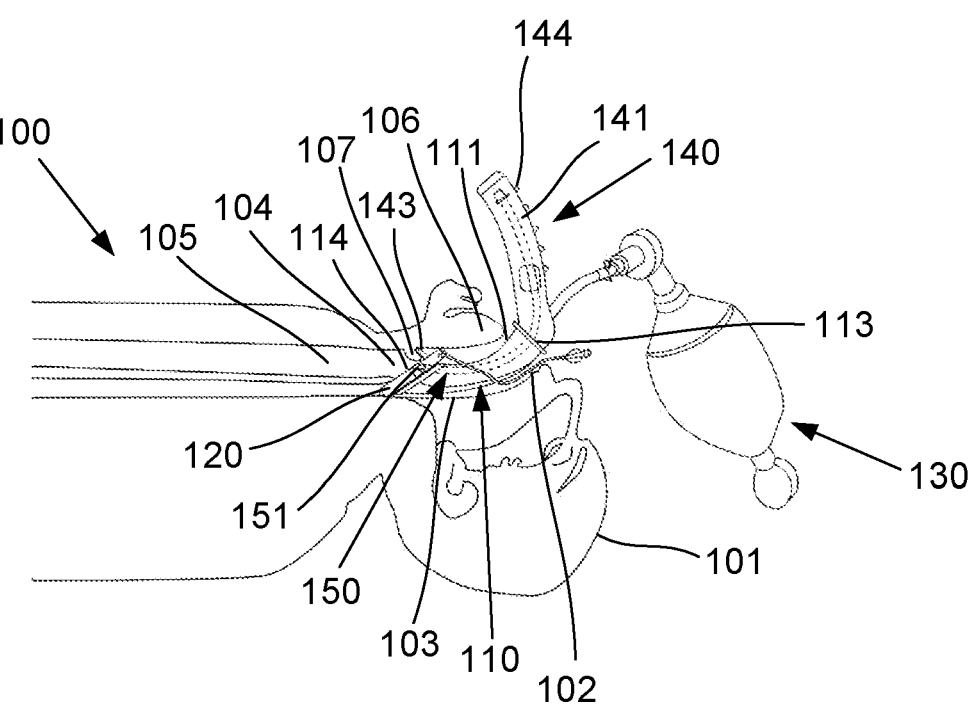
Figure 1F:
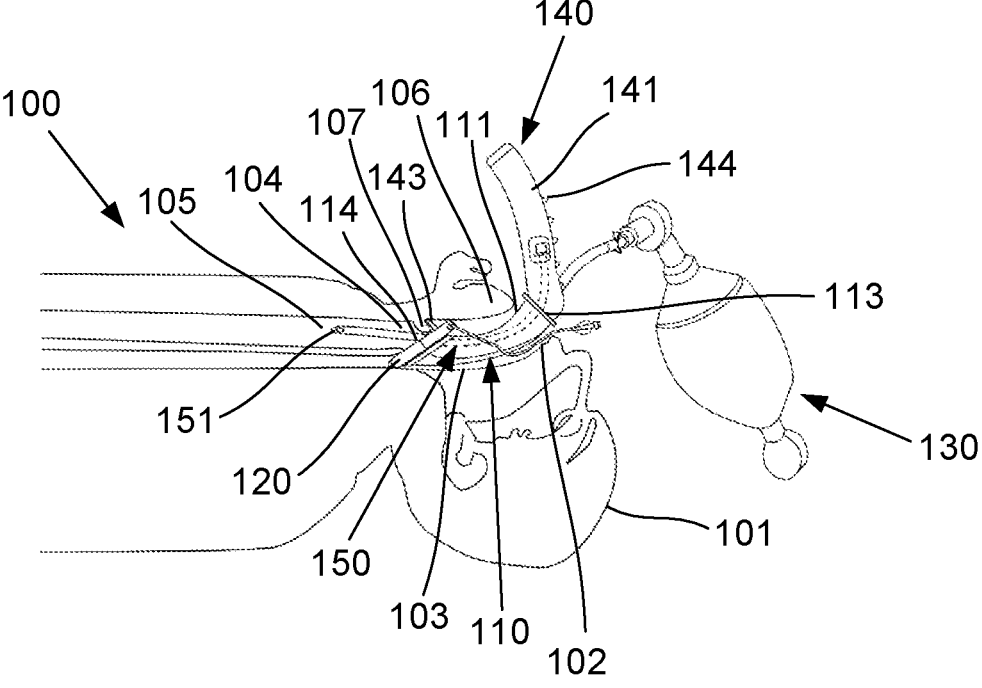

Turning to FIG. 1C, once the LMA intubation guide 110 has been inserted so that the subject's larynx 104 is covered by the laryngeal mask 120, the subject 100 may be ventilated using the ventilation airway 115 of the LMA intubation guide 110. Typically, this will involve connecting a ventilator 130 to the ventilation airway 115 so that a ventilation gas can be supplied via the ventilation airway to a delivery point proximate to the laryngeal mask 120.

With regard to the further details of the LMA intubation guide shown in FIGS. 2A to 2D, the ventilator 130 may be connected to the ventilation port 211 at the proximal end of the ventilation airway 115, and the ventilation gas supplied by the ventilator 130 will be delivered to the subject 100 via the ventilation aperture 212 at the distal end of the ventilation airway 115. In this example, the ventilation aperture 212 is located just inside the mask cuff 223 of the laryngeal mask 120 and may be configured to direct the ventilation gas towards the larynx 104 of the subject.

It should be appreciated that any suitable type of ventilator 130 may be used for ventilating the subject 100. In this example, a manual bag-valve type ventilator 130 is used and is connected to the ventilation port 211 of the ventilation airway 115 using a suitably configured ventilator connector. The ventilator connector will typically be a standard/universal connector type. The ventilator will generally be located outside the mouth of the subject.

Whilst the depicted examples show a ventilator 130 in the form of a manual bag-valve mask ventilator connected directly to the ventilation airway 115, the ventilator 130 may alternatively be in the form of a powered mechanical ventilator, for example. In some embodiments, a more distant ventilator unit may be connected to the ventilation port 211 by a length of flexible tubing, or the like.

The process of ventilating the subject 100 using the ventilation airway 115 may include oxygenating the subject using the ventilation airway 115, such as by supplying oxygen gas from an oxygenation source to the ventilation port. In some cases, 100% oxygen may be supplied or air may be supplied at lower oxygen percentages. Nevertheless, it should be appreciated that oxygenation is not essential and the ventilation may be provided using atmospheric air without added oxygen. This may depend on whether a separate pressurised oxygen source is available, which may not be the case in some circumstances.

Ventilation of the subject 100 can continue to be performed as shown in FIG. 1C as required, and in this regard it will be appreciated that the LMA intubation guide 110 may be used in a similar manner as a traditional laryngeal mask airway device. This ventilation can continue until indefinitely until the user decides to proceed with the endotracheal intubation of the subject. For instance, the user may wish to continue ventilation until a desired blood oxygen saturation level is achieved, before intubating the subject. Alternatively, the LMA intubation guide 110 may be inserted by another user and the subject may be ventilated while waiting for an intubation specialist to become available for performing the intubation of the subject.

In some embodiments, the LMA intubation guide 110 may include a closure for covering the proximal opening 113, and thus preventing the escape of ventilation gas supplied to the subject via the ventilation airway through the passageway and out of the proximal opening 113 while the subject 100 is being ventilated. In this example, a closure is provided in the form of a cap 116 that effectively seals the proximal opening 113. Typically the cap 116 will remain in place for sealing the proximal opening 113 during the initial insertion of the LMA intubation guide 110 and as ventilation commences and continues as shown in FIG. 1C. However, the use of a closure may not be essential since ventilation gas may be supplied directly to the larynx such that the escape of some ventilation gas may not be critical. Alternative forms of closures may also be provided, such as movable seals as will be discussed in further detail below.

Turning to FIG. 1D, while the subject 100 is being ventilated, an intubation device 140 will be provided for performing endotracheal intubation of the subject 100. As mentioned, above, in this example the intubation device 140 is a single handed intubation device and includes a handle portion 141 connected to the blade portion 142, for allowing the user to hold the intubation device 140 and move the blade portion 142 and the distal tip 143 relative to the subject's anatomy. This form of intubation device 140 includes a channel for receiving an endotracheal tube 150, and a tube movement mechanism in the handle portion 141 for moving the endotracheal tube 150 through the channel to thereby advance the endotracheal tube 150. In this case, the tube movement mechanism includes a thumb interface 144 for allowing the user to operate the tube movement mechanism using a thumb of the hand that is holding the intubation device, to thereby allow the user to hold the intubation device 140 and advance the endotracheal tube 150 in an endotracheal intubation procedure using a single hand.

In this example, the cap 116 is also removed prior to inserting the blade portion 142 through the passageway 112 as also indicated in FIG. 1D. However, it should be appreciated that the use of a closure in the form of a removable cap 116 is not essential. In other embodiments, alternative forms of closures may be used. For instance, other examples of the LMA intubation guide 110, such as the embodiment shown in FIG. 8, may include a seal 801 covering the proximal opening 113. The seal 801 may be configured to normally be in a closed position for sealing the proximal opening 113 and being moveable to an open position when the blade portion 142 of the intubation device 140 is inserted through the passageway 112. Thus, the blade portion 142 may be inserted through the seal 801 of the proximal opening 113 without requiring the removal of a closure. In other embodiments, no closure may be provided at all, if adequate ventilation of the subject can be achieved despite some leakage of ventilation gas from the proximal opening 113.

In preferred embodiments, the seal 801 will be biased towards the closed position, such that the seal 801 returns towards the closed position when the blade portion 142 of the intubation device 140 is removed from the passageway 112 after the procedure. The seal 801 may be configured to form a partial seal surrounding at least one of the blade portion 142 of the intubation device 140 and the endotracheal tube 150, thereby helping to reduce the escape of ventilation gas that may otherwise pass around the blade portion 142 or endotracheal tube 150 in use.

In any event, with regard to FIG. 1E, while ventilation of the subject 100 continues, the blade portion 142 of the intubation device 140 is inserted into the passageway 112 of the LMA intubation guide 110, through the proximal opening 113.

Figure 4A:
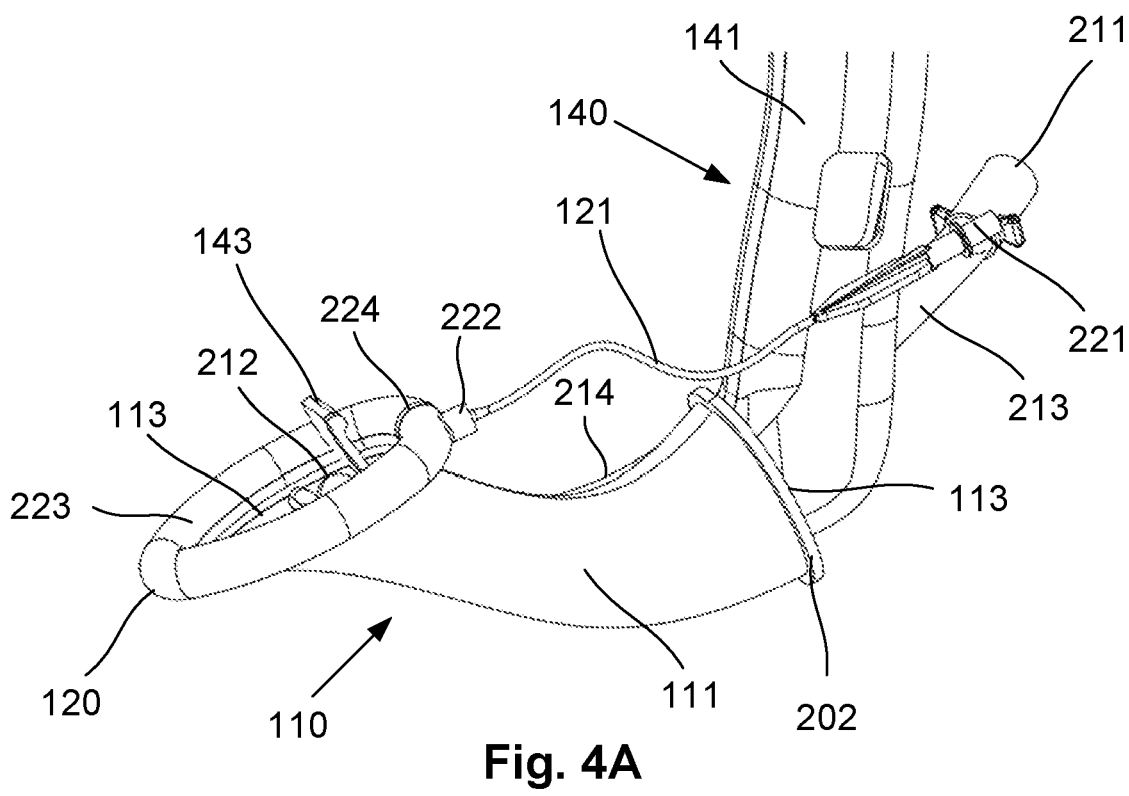
FIG. 4A is a perspective view of the LMA intubation guide of FIGS. 3A and 3B, with a blade portion of an intubation device inserted into the passageway of the LMA intubation guide.
Figure 4B:
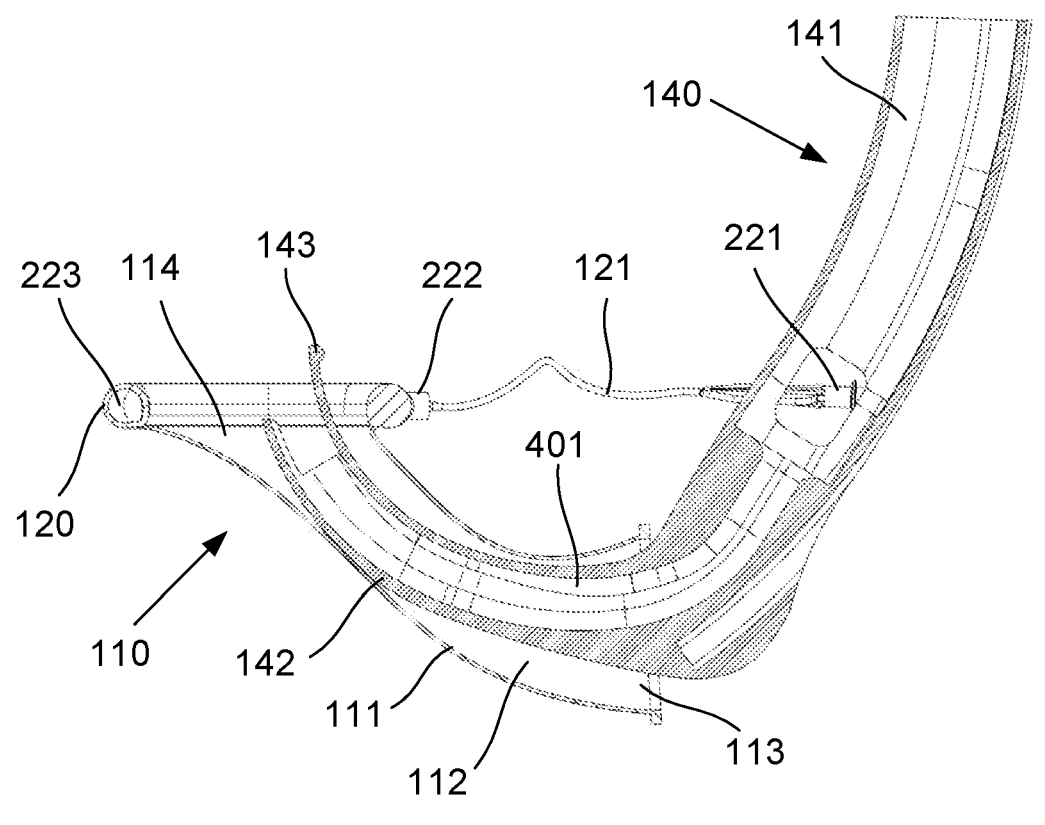
FIG. 4B is a cross section view of the LMA intubation guide and the inserted blade portion of the intubation device of FIG. 4A.

The blade portion 142 of the intubation device 140 is passed through the passageway 112 of the LMA intubation guide 110 to position a distal tip 143 of the blade portion 142 proximate to the larynx 104 of the subject 100. Typically, the distal tip 143 will protrude through the distal opening 114 and laryngeal mask 120, as can be seen in FIGS. 4A and 4B which provide detailed views of the positioning of the blade portion 142 of the intubation device 140 relative to the LMA intubation guide 110.

The specific positioning of the distal tip 143 will depend of the particular configuration of the blade, but typically the distal tip 143 will be positioned around the epiglottis 107 and moved as required to expose the glottis of the subject. The distal tip 143 may engage with the vallecula inside the subject's trachea 105. As the blade portion 142 is moved, this may result in some movement of the LMA intubation guide 110 relative to the subject's mouth 102 and tongue 106.

Now turning to FIG. 1F, once the distal tip 143 has been moved to an appropriate position to allow endotracheal intubation, the endotracheal tube 150 is advanced along the blade portion 142 of the intubation device 140 through the passageway 112 of the LMA intubation guide 110, into the trachea 105 of the subject. It will be appreciated that the use of a single handed intubation device 140 allows the endotracheal tube 150 to be advanced by the user operating the thumb interface 144 using the thumb of the same hand holding the device. However, if a different form of intubation device that does not facilitate single handed intubation is used, the endotracheal tube 150 may be advanced manually, in a generally conventional manner.

In any event, as mentioned above, the entire endotracheal intubation procedure including inserting the intubation device 140 and advancing the endotracheal tube 150 into the trachea 105 may be performed while the subject 100 is ventilated, thereby avoiding the potentially risky period without ventilation that takes place in conventional endotracheal intubation procedures. Accordingly, the method may be used to allow endotracheal intubation to be performed without the time pressure that medical professionals often face in conventional endotracheal intubation procedures. It will be appreciated that this can greatly improve the likelihood of successful intubation, even in traditionally difficult circumstances.

The endotracheal tube 150 will typically be a standard type of endotracheal tube and may include a balloon cuff (not shown), which can be inflated once the endotracheal tube 150 has been advanced into the desired position. It will be appreciated that the inflated balloon cuff can help to retain the endotracheal tube 150 in place in the subject's trachea 105.

Figure 1G:
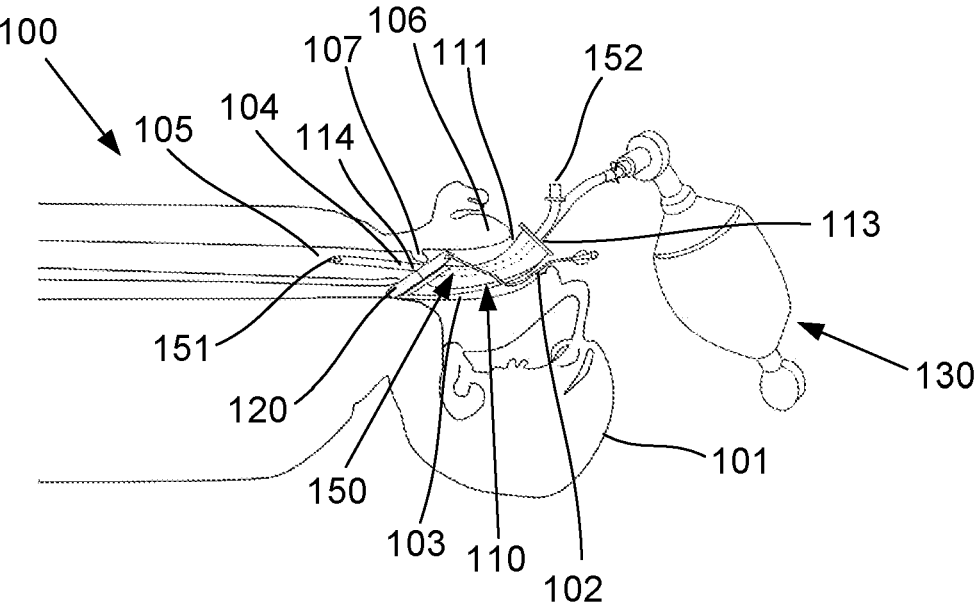

After the endotracheal tube 150 has been advanced into the trachea 105 of the subject 100 (and the balloon cuff inflated, if provided on the endotracheal tube 150), the intubation device 140 may be removed while leaving the endotracheal tube 150 in place in the trachea 105 as shown in FIG. 1G. This may be performed by withdrawing the blade portion 142 of the intubation device 140 from the LMA intubation guide 110, with the endotracheal tube 150 remaining in position as shown in FIG. 1G. At this stage, the LMA intubation guide 110 will still be left in place and ventilation of the subject 100 will still be provided using the ventilator 130 via the ventilation airway 115 of the LMA intubation guide 110.

Figure 1H:
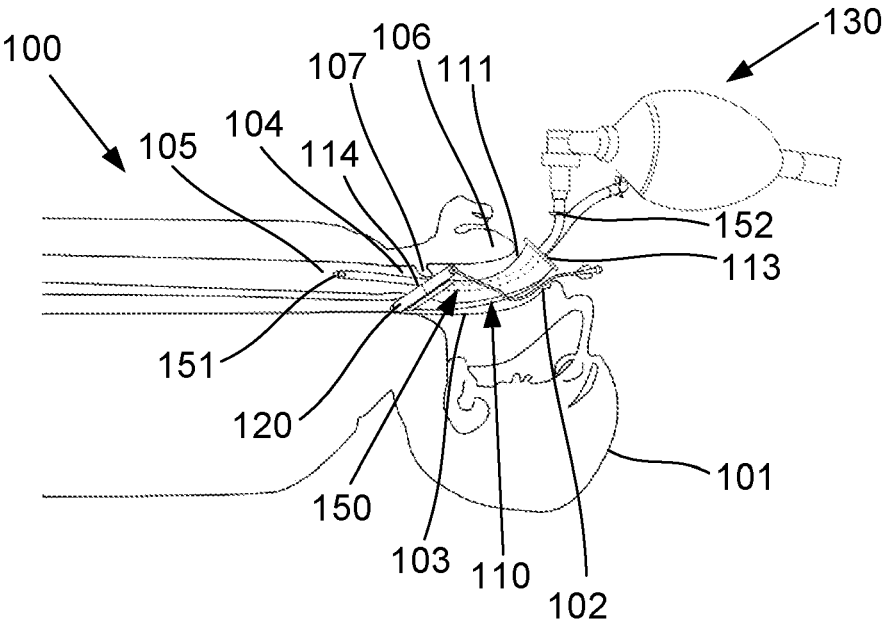

Then, as shown in FIG. 1H, the endotracheal tube 150 can be coupled to a ventilation source and used to provide ventilation to the subject 100 instead. The ventilation source may be the same as that used to provide ventilation using the ventilation airway 115, or may be a different ventilation source. In this case, the ventilator 130 is disconnected from the ventilation airway 115 and immediately connected to a connector 152 at the proximal end of the endotracheal tube 150 so that ventilation will be provided via the endotracheal tube 150 with minimal interruption.

In some cases it may be preferable that ventilation using the endotracheal tube 150 is established before ceasing ventilation using the ventilation airway 115, so as to ensure that the subject is continuously ventilated, which may require the use of a second ventilation source. In some examples, it may be desirable to confirm effective ventilation using the endotracheal tube 150 before disconnecting the ventilator 130 from the ventilation airway 115, and if this is not the case, ventilation may be continued using the ventilation airway 115 while the user repositions the endotracheal tube 150 to allow effective ventilation to be achieved. However, this may not be essential especially if the operator can otherwise confirm that the endotracheal tube 150 has been properly deployed and the duration without ventilation while switching from ventilation via the ventilation airway 115 to ventilation via the endotracheal tube 150 is kept to a minimum.

Once ventilation via the endotracheal tube 150 has been established as shown in FIG. 1H, the LMA intubation guide 110 may be removed from the mouth 102 of the subject 100, leaving the endotracheal tube 150 in position for continued ventilation. In embodiments of the LMA intubation guide 110 having a laryngeal mask 120 with an inflatable mask cuff 223, the mask cuff 223 may optionally be deflated at this stage.

Figure 1I:
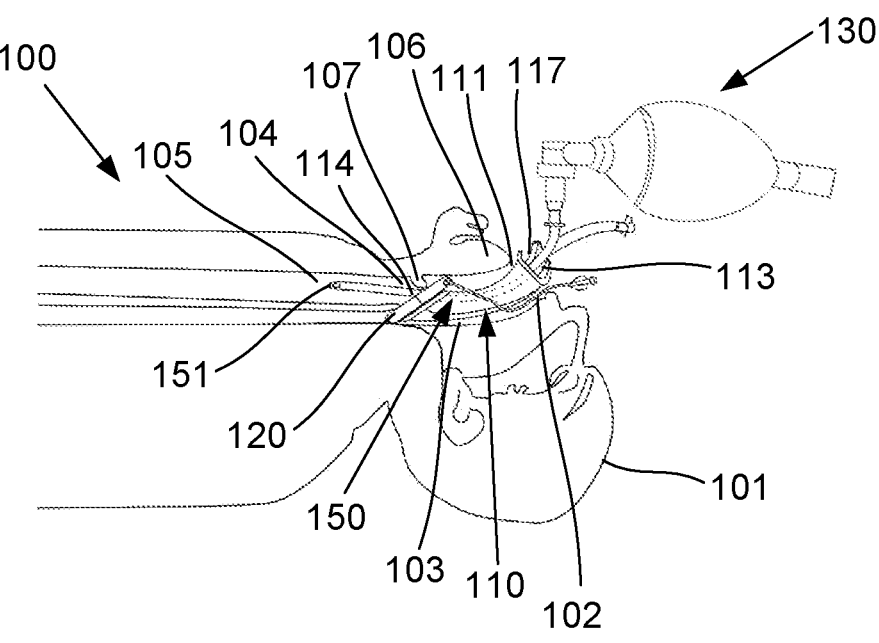

In some embodiments, the LMA intubation guide 110 may be configured to be broken along the passageway 112 and the laryngeal mask 120 to allow its removal, as shown in FIG. 1I. For instance, with regard to the example LMA intubation guide 110 shown in FIGS. 2A to 2F, this may be facilitated by defining a break line 117 in the body 111, further details of which will be described in due course. In the present embodiment, in which the laryngeal mask 120 includes a mask cuff 223, a partition 224 may also be provided in the mask cuff 223 as an effective extension of the break line 117. It will be appreciated that, when the mask cuff 223 is of an inflatable type, this partition 224 may represent air-tight end walls of the inflatable volume of the mask cuff 223.

Figure 1J:
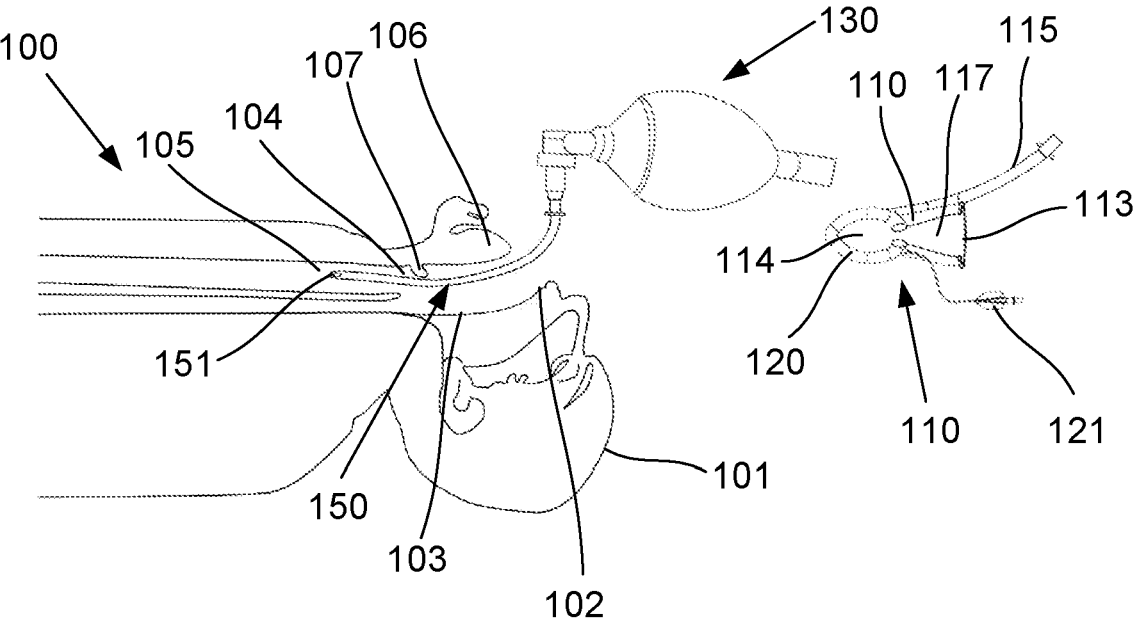
Figure 5B:
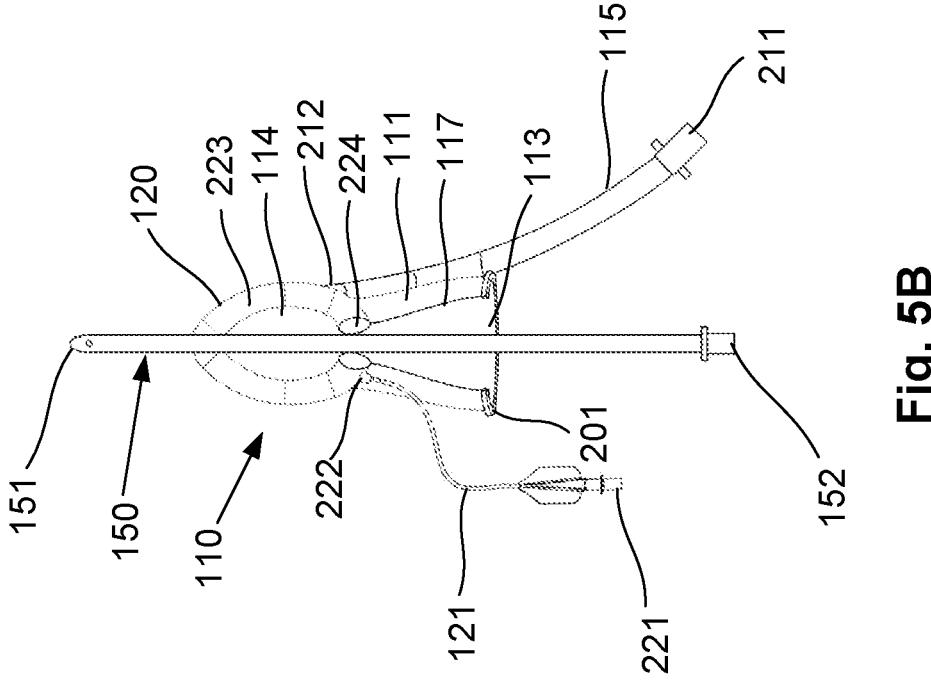
FIG. 5B is a bottom view of the LMA intubation guide and endotracheal tube of FIG. 5A, with the LMA intubation guide broken for removal of the endotracheal tube.
Figure 5A:
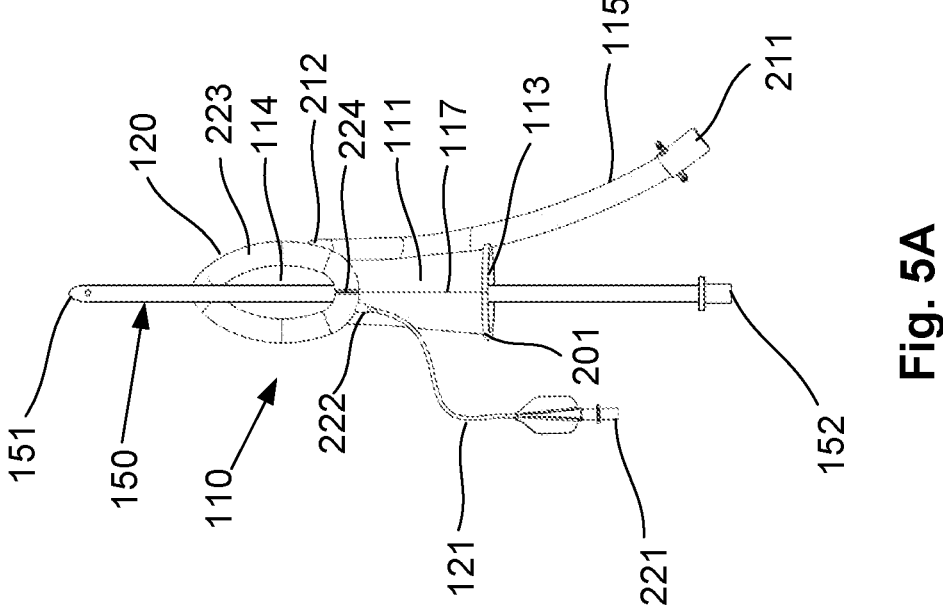
FIG. 5A is a bottom view of the LMA intubation guide of FIGS. 3A and 3B, with an endotracheal tube advanced through a passageway of the LMA intubation guide.

In any event, when using such an LMA intubation guide 110, the method may include breaking the LMA intubation guide 110, as per FIG. 1I, to allow the LMA intubation guide 110 to be removed while the endotracheal tube 150 remains in place, as shown in FIG. 1J. FIGS. 5A and 5B show detailed views of the LMA intubation guide 110 before and after being broken, with an endotracheal tube 150 extending through the passageway 112, to thereby illustrate how this will allow the LMA intubation guide 110 to be removed whilst leaving the endotracheal tube 150 in its deployed position.

It will be appreciated that this approach of breaking the LMA intubation guide 110 may avoid the need to pass the intubation guide 110 over the tube fitting at the proximal end of the intubation tube 150 and the need to disconnect the proximal end of the endotracheal tube 150 which would undesirably interrupt ventilation of the subject using the endotracheal tube 150. This can also avoid the risk of unintentionally displacing the endotracheal tube 150 from its delivered position and potentially losing the secure airway during removal of the LMA intubation guide 110.

In alternative examples, the LMA intubation guide 110 may include cutting marks (not shown) and be configured to be cut along the passageway 112, by following the cutting marks. It will be appreciated that this will facilitate a similar functionality for facilitating removal of the LMA intubation guide 110 as discussed above, without the need to provide breakable portions in the construction of the LMA intubation guide 110, but with the added requirement for using a cutting tool.

The LMA intubation guide 110 may be designed so that the passageway 112 is fitted to the blade portion 142 of the intubation device 140 without having to build in an allowance for the tube fitting. As will be discussed further in due course, this can help to reduce leakage of ventilation gas around the blade portion 142 during the procedure.

It will be appreciated that the above method provides a new technique for allowing endotracheal intubation to be performed on a subject while a temporary airway is provided using the LMA intubation guide 110. In difficult intubation scenarios, the LMA intubation guide 110 may be inserted to establish the temporary airway and ventilate the subject for as long as required to stabilise the subject's condition before actually performing the endotracheal intubation procedure. In some circumstances, the LMA intubation guide 110 may be used to provide a temporary airway for longer periods of time until suitably skilled personnel are available to perform the endotracheal intubation procedure.

In any event, in view of the above description of the method, it will be appreciated that the ability to perform the ventilated intubation procedure will be enabled by the particular design of the LMA intubation guide 110, which will now be described in further detail with regard to FIGS. 2A to 2F.

As discussed above, the LMA intubation guide 110 includes an elongate body 111 defining a passageway 112 extending between a proximal opening 113 and a distal opening 114. The passageway 112 is configured for receiving a blade portion 142 of an intubation device 140. The LMA intubation guide 110 also includes a laryngeal mask 120 at the distal opening 114. The laryngeal mask 120 is for covering the larynx 104 of the subject 100. The LMA intubation guide 110 further includes a ventilation airway 115 extending at least partially along the body 111. The ventilation airway 115 includes a ventilation port 211 at a proximal end of the ventilation airway 115 for connection to a ventilator 130, and a ventilation aperture 212 at a distal end of the ventilation airway 115 for allowing fluid communication between the ventilation airway 115 and the passageway 112 proximate to the laryngeal mask 120.

As mentioned previously, the LMA intubation guide 110 is configured for insertion into a mouth 102 of the subject 100 so that the proximal opening 113 is positioned proximate to the mouth 102 of the subject and the laryngeal mask 120 is positioned proximate to a larynx 104 of the subject, to thereby allow the blade portion 142 of the intubation device 140 to be inserted into the passageway 112 of the LMA intubation guide to allow intubation of the subject 100 using an endotracheal tube 150 through the passageway, while the subject 100 is ventilated using the ventilation airway 115.

It should be understood that the LMA intubation guide 110 will allow ventilation of the subject 100 via the ventilation airway 115 after it is inserted and prior to endotracheal intubation being performed. This ventilation can include oxygenation, and can continue for a prolonged time if required. In some cases the LMA intubation guide 110 may be only used for ventilation, or may be used for ventilation up until the moment it is decided that endotracheal intubation required. It should therefore be appreciate that the LMA intubation guide may be configured to allow ventilation of the subject independently of intubation of the subject being performed.

The elongate body 111 of the LMA intubation guide 110 may be curved as depicted in the example of FIGS. 2A to 2F. Such a curved configuration may be provided so that the LMA intubation guide 110 can better conform to the mouth 102 and airway anatomy of the subject 100 in use. However, it is not essential that the LMA intubation guide 110 be curved.

The LMA intubation guide 110 may be formed from different materials having different levels of flexibility depending on requirements. For instance, embodiments of the LMA intubation guide 110 may be formed from a relatively flexible material such that the LMA intubation guide 110 may be allowed to at least partially deform in order to conform to the natural curvature of the mouth 102 and airway anatomy of the subject in use. On the other hand, embodiments of the LMA intubation guide 110 may be formed from a relatively inflexible material, where a curvature of the body 111 will need to be selected to conform to the subject's anatomy without relying on substantial deformation of the intubation guide 110.

It will be appreciated that the LMA intubation guide 110 may serve to allow the blade portion 142 of the intubation device 140 to be inserted into the airway of the subject 100 without interference with the subject's tongue and other anatomical structures which may otherwise obstruct the insertion of the blade portion 142 in use. This is especially advantageous since the LMA intubation guide 110 may prevent direct visualisation during insertion of the blade portion 142. It should be understood that the LMA intubation guide 110 will typically act to hold the tongue of the subject and typically to depress the tongue, i.e. to urge the tongue downwardly. This may depend on the particular shape and configuration of the LMA intubation guide 110, including the curvature and flexibility as discussed above.

The proximal opening 113 of the LMA intubation guide 110 is configured to allow the blade portion 142 to be inserted into the passageway 112 of the intubation guide 110 through the proximal opening 113. Preferably, the LMA intubation guide 110 will be designed to suit the intubation device 140 and particularly its blade portion 142. The intubation device 140 and endotracheal tube 150 that are used in the procedure may not necessarily be provided with any specific adaptations for use in a ventilated endotracheal intubation procedure as described above. Accordingly, the LMA intubation guide 110 may be provided separately to the intubation device 140 and endotracheal tube 150, provided the correct type of intubation device 140 and respective blade portion 142 are selected for the LMA intubation guide 110.

As mentioned previously, the laryngeal mask 120 at the distal opening 114 of the LMA intubation guide 110 is configured for covering the larynx 104 of the subject 100. The ventilation airway 115 includes a ventilation port 211 at a proximal end of the ventilation airway 115 for connection to a ventilator, and a ventilation aperture 212 at a distal end of the ventilation airway 115 for allowing fluid communication between the ventilation airway 115 and the passageway 112 proximate to the laryngeal mask 120.

Further preferred or optional features of the LMA intubation guide 110 and their associated advantages will now be described.

The LMA intubation guide 110 will typically be formed from a suitable medical grade plastic material, and in some embodiments may be transparent to allow visualisation of the subject's anatomy in use. However, the use of a transparent material may be unnecessary if a laryngoscope with a video capability is used.

The basic construction of the laryngeal mask 120 may be similar to conventional laryngeal masks of known laryngeal mask airway devices. The laryngeal mask 120 will typically include a mask cuff 223 that forms a seal around the subject's larynx 104. The cuff will usually surround the proximal opening 113 of the LMA intubation device 110.

As mentioned previously, the mask cuff 223 may be of the inflatable type, in which case the mask cuff 223 will typically include an airtight chamber formed from a flexible material. The mask cuff 223 may be inflated using an inflation conduit 121, which may be connected to the chamber of the mask cuff 123 via an inflation port 222, and which may include a suitably configured inflation connector 221 for connection to an inflation source, such as an air-filled syringe, an external air supply line, or the like. The inflation conduit 121 may be formed from thin tubing and should be of a length that can extend from the laryngeal mask 120, through the subject's pharynx 103 and mouth 102 to thereby allow access to the inflation connector 221 at a convenient position outside of the mouth 102 after insertion of the LMA intubation guide 110, as shown for instance in FIG. 1B.

The ventilation aperture 212 of the ventilation airway 115 will typically be located inside the passageway, proximate to laryngeal mask 120. In some examples, the ventilation aperture 212 may be provided directly inside the laryngeal mask 120, or otherwise near distal opening 114 of the LMA intubation guide 110. In this case, the ventilation aperture 212 is located adjacent to the mask cuff 223 of the laryngeal mask 120, which can allow ventilation gas to be supplied close to the larynx 104 of the subject 100.

The ventilation airway 115 may be offset from the passageway 112 of the LMA intubation guide 110. In this case, the ventilation airway 115 is offset laterally relative to a central plane of the LMA intubation guide 110 that is aligned with a sagittal plane of the subject when the laryngeal mask 120 covers the larynx 104 of the subject 100. However, this positioning is not essential and different embodiments may have different ventilation airway 115 locations relative to other features of the LMA intubation guide 110.

In some embodiments, the ventilation aperture 212 may be particularly configured to direct a flow of ventilation gas towards the larynx 104 of the subject 100. This may help to ensure that ventilation gas is less likely to escape from the proximal opening 113 of the LMA intubation guide 110, in the case of an imperfect closure or seal, or in the absence of a closure.

With regard to the example show in FIGS. 2A to 2F, the ventilation airway 115 may include an airway body portion 214 that extends along the body 111, and may also include an airway conduit portion 213 that extends away from the proximal opening 113. Preferably, at least the airway body portion 214 is formed integrally with the body 111. Thus, the ventilation airway 115 may extend alongside the passageway in a close parallel arrangement.

Preferably, the LMA intubation guide 110 will be configured to allow the subject 100 to be ventilated using the ventilation airway 115 without allowing ventilation gas to escape from the proximal opening 113 before and during inserting the blade portion 142 of the intubation device 140. In some implementations, this can be achieved by providing the proximal opening 113 with a closure for covering the proximal opening 113, such that the closure may be kept in place during ventilation but removed prior to inserting the blade portion 142 through the proximal opening 113.

Following insertion, the blade portion 142 may be sufficient to substantially prevent the escape of gas from the proximal opening 113. Once the intubation procedure is completed, ventilation can continue via the endotracheal tube. The closure may thus be provided in the form of a removable cap or plug which may be applied to the proximal opening 113 as required using a range of different possible interfaces, such as a threaded connection, an interference fit, or the like. Alternatively, the closure may be provided in the form of a movable cover such as a hingedly attached barrier that can be pushed out of the way upon insertion of the blade portion 142.

Figure 3A:
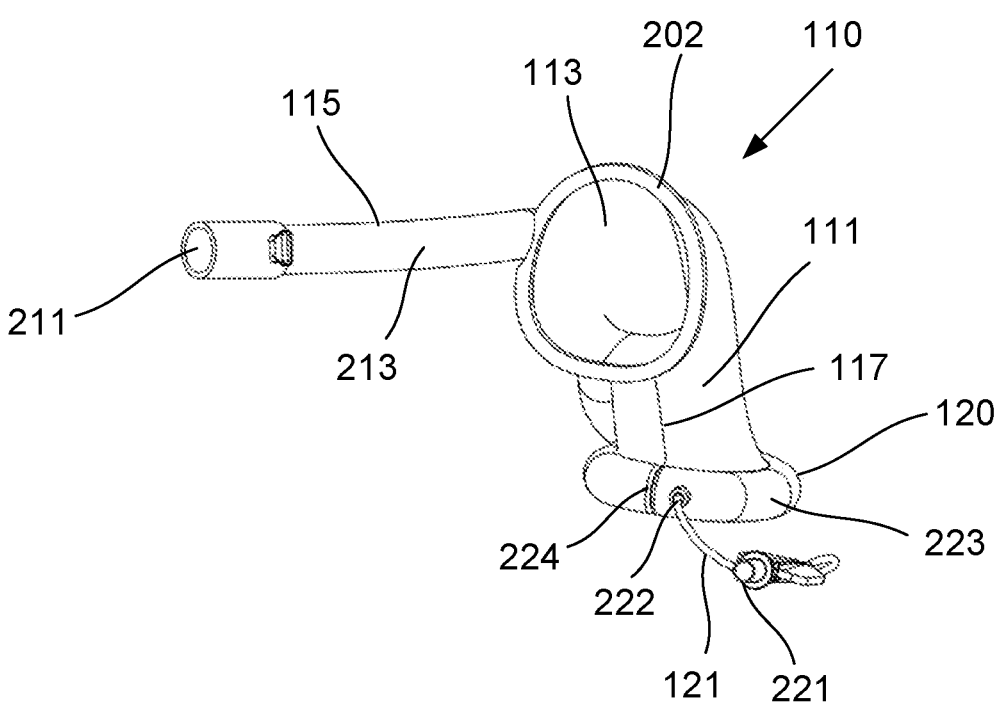
FIGS. 3A and 3B are perspective views of the LMA intubation guide of FIGS. 2A and 2B, with a cap removed.
Figure 3B:
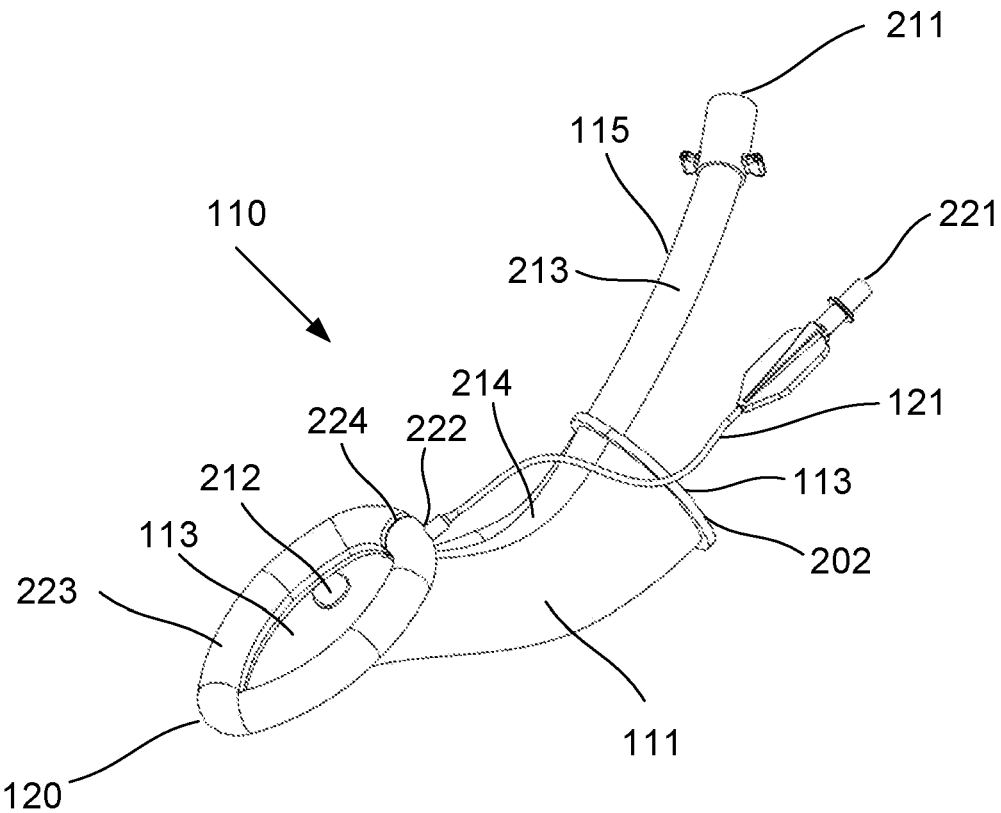

In the present example, the closure is provided in the form of a removable cap 116 that covers the proximal opening 113 and which can be removed to allow insertion of the blade portion 142 through the proximal opening 113 as required, as indicated in FIG. 1D. In this case, the cap 116 engages with a rim 201 surrounding the proximal opening 113 in an interference fit. The cap 116 may include a pull tab 202 or a similar feature for allowing an operator to remove the cap 116 by gripping and pulling the tab 201. FIGS. 3A and 3B show additional views of the LMA intubation after the cap 116 has been removed.

Figures 8, 9:
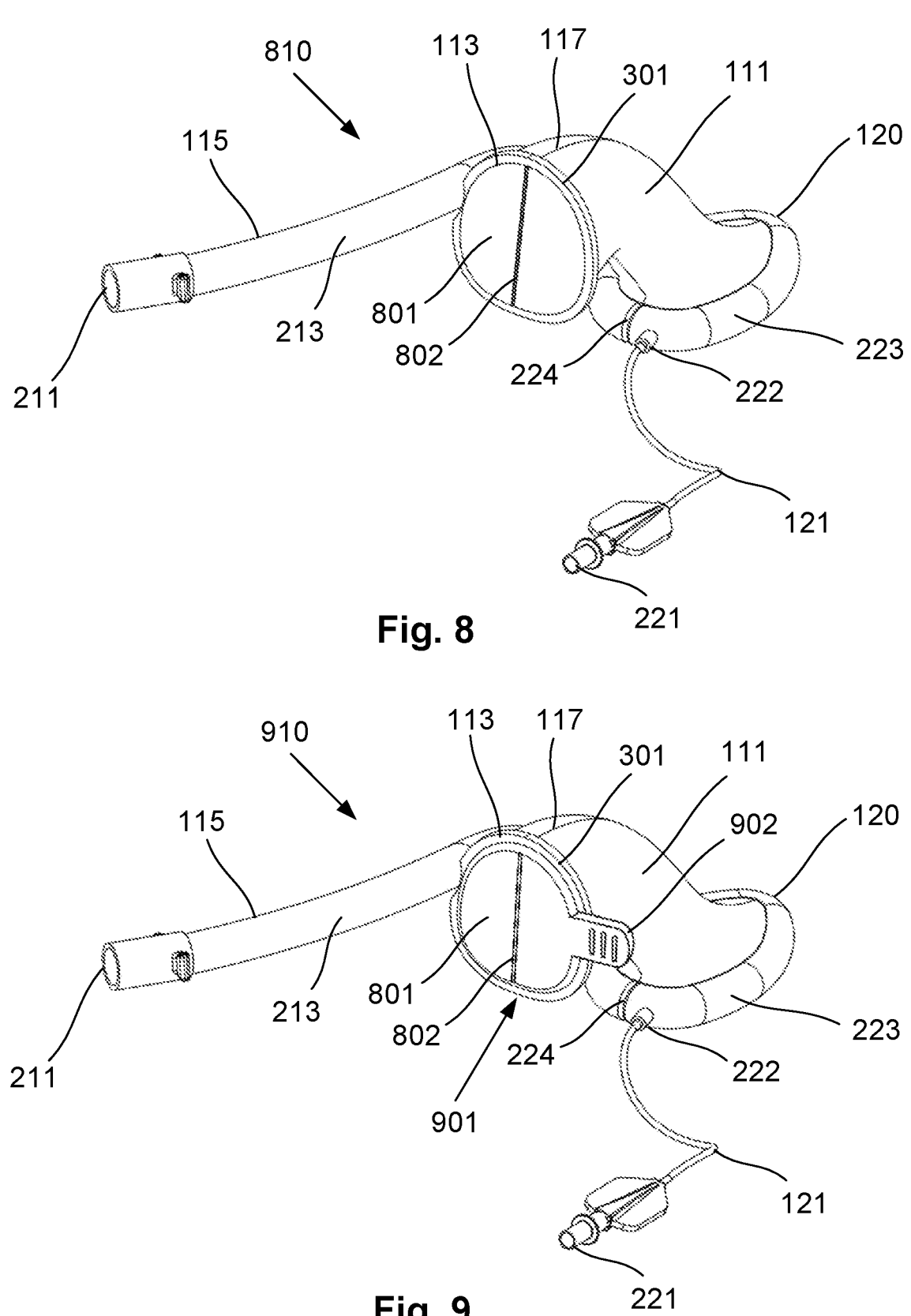
FIG. 8 is a perspective view of a third example of an LMA intubation guide having a membrane seal for sealing the proximal opening.
FIG. 9 is a perspective view of a third example of an LMA intubation guide having a separate removable cap-seal for sealing the proximal opening.

In some implementations, such as in the example of an LMA intubation guide 810 as shown in FIG. 8, the LMA intubation guide 810 may include a seal 801 covering the proximal opening 113. The seal 801 may be configured to be normally in a closed position for sealing the proximal opening 113 and may be moveable to an open position when the blade portion 142 of the intubation device 140 is inserted through the proximal opening 113. Turning back to FIG. 1E, it will be appreciated that, when the blade portion 142 of the intubation device 140 is first inserted into the proximal opening 113, this may cause the seal 801 in the proximal opening 113 to move from the closed position to the open position, to thereby permit the blade portion 142 to pass through the proximal opening 113.

As mentioned above, the seal 801 may be moveable from a normally closed position (as shown in FIG. 8) to an open position when the blade portion 142 of the intubation device 140 is inserted through the proximal opening 113. In some embodiments, the seal 801 may include at least one resilient membrane configured to deform in response to the blade portion 142 being urged against the seal 801, to thereby define an opening for receiving the blade portion 142.

In one example, the seal 801 may include two or more resilient membranes that are each supported around a respective part of a perimeter of the proximal opening 113 and that each include a respective unsupported edge 802. The respective unsupported edges 802 may at least partially overlap in the closed position and separate to define the opening in the open position. Although overlapping edges 802 are preferred for more effective sealing, in some examples the edges 802 may be abutted in the closed position without any overlap.

In other examples, the seal 801 may include two or more resilient membranes that are supported around the perimeter of the proximal opening 113. The respective aperture of each resilient membrane may differ from the apertures of other resilient membranes in shape, location or orientation. In other words, the seal 801 may include multiple fully supported membranes with apertures such as slits that do not align or overlap, to thereby provide an enhance sealing effect.

In another example, the seal 801 may include a single resilient membrane that is supported around a perimeter of the proximal opening 113. The single resilient membrane may include an aperture that is substantially closed in the closed position and that stretches to define the opening in the open position. For instance, in some embodiments, the aperture may be a slit. In other embodiments, the aperture may be a pinhole, or may have any other geometry selected to allow a suitable opening to be formed for receiving the blade portion 142 of the intubation device 140. For instance, the aperture could be cross shaped or H shaped.

The at least one resilient membrane may be formed from any suitable membrane material, although typically a thin, flexible polymer material will be used. It may also be desirable to form the membranes from a transparent material as mentioned above for the LMA intubation guide 110.

It will be appreciated that, when the blade portion 142 is received in the proximal opening 113 (for example, as shown in FIGS. 4A and 4B), the seal 801 may be in the open configuration but may still provide effective sealing around the blade portion 142 to substantially prevent the escape of ventilation gas around the blade portion 142 during the intubation procedure. The degree of sealing or leakage will depend on the design of the seal 801 and also the design of the blade portion 142. For instance, if the seal 801 is configured to stretch around the blade portion 142 in the open position this may form a substantially airtight seal even when the blade portion 142 extends through the proximal opening 113.

It will be appreciated that some leakage could still take place via the channel 401 that extends through the blade portion 142 to allow delivery of the endotracheal tube 150, especially in open channel designs as depicted. In some examples, the intubation device 140 may be designed to include a channel seal (not shown) as described in WO/2016/090435A1. Such a channel seal can be used to prevent the escape of gas from the ventilation port 122 along the channel 401. However, this is not essential, and in some intubation device 140 designs the endotracheal tube 150 may fit in the channel 401 so as to not provide a significant leakage path and the seal 801 may conform to the blade portion sufficiently well to prevent substantial leakage.

FIG. 9 shows an alternative embodiment of the LMA intubation guide 110, in which a separate removable cap-seal part 901 may be provided in place of the cap 116 to provide a seal 801 similar to that shown previously. The cap-seal part 901 may also have a slightly different design compared to the previous cap 116, particularly in that the cap-seal part 901 may have a removal tab 902 extending to a side of the cap-seal part 901 to allow removal with a peeling action as opposed to a pulling action.

Furthermore, the cap-seal part 901 may include an integral seal 801 for covering the proximal opening 113, the seal normally being in a closed position for sealing the proximal opening 113 and being moveable to an open position when the blade portion 142 of the intubation device 140 is inserted through the proximal opening 113, thereby functioning in a similar fashion to the seal 801 of the earlier described embodiment of the shielded intubation guide 810 in FIG. 8. The seal 801 of the cap-seal part 901 may include a seal membrane having and one or more slits 802 or other orifices formed in it to thereby permit the blade portion 142 upon insertion.

As per the cap 116 and seal 801 described above, the cap-seal part 901 is intended to prevent the escape of ventilation gas from the proximal opening 113 while the subject 100 is being ventilated. Preferably this can be achieved even while a laryngoscope blade and endotracheal tube are positioned inside the proximal opening 113, by partially sealing the proximal opening 113 around any inserted object. If the laryngoscope blade and endotracheal tube are removed, the seal will return to its original closed position to thereby reform a full seal.

It should be appreciated that, by providing the seal 801 in a separate cap-seal part 902, this allows the cap-seal part 902 to be formed from a suitable resilient material, such as a silicone or rubber material, whereas the LMA intubation guide 910 can be formed from a different material. This can greatly simplify manufacture of the LMA intubation guide 910.

It should also be appreciated that the use of a removable cap may be especially desirable for use with a non-video or direct vision laryngoscope, to thereby allow the user to have an unobstructed visual line of sight into the proximal opening 113 and through the passageway 112.

It will be appreciated that the LMA intubation guide 110 may be allowed to move relative to the subject's anatomy as the blade portion 142 of the intubation device 140 is inserted through the passageway 112 and specifically as the distal tip 143 is moved to a suitable position to allow the endotracheal tube 150 to be advanced through the larynx 104 into the trachea 105 of the subject.

Figures 2A, 2B:
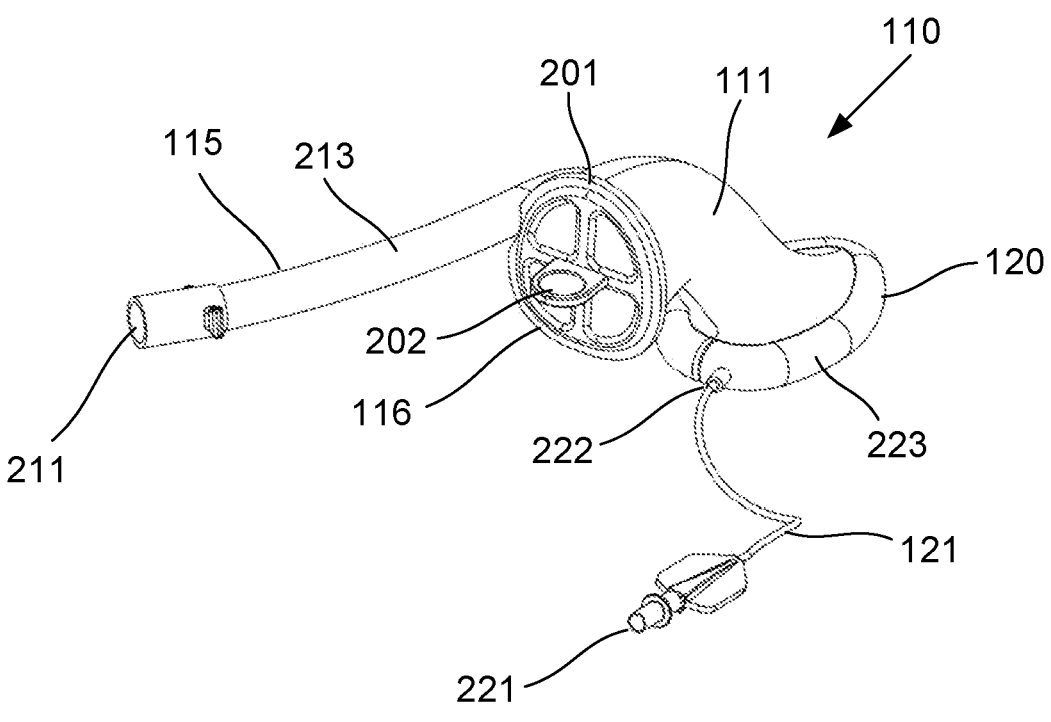
FIGS. 2A and 2B are perspective views of the first example of the LMA intubation guide of FIGS. 1A to 1J.
Figure 2C:
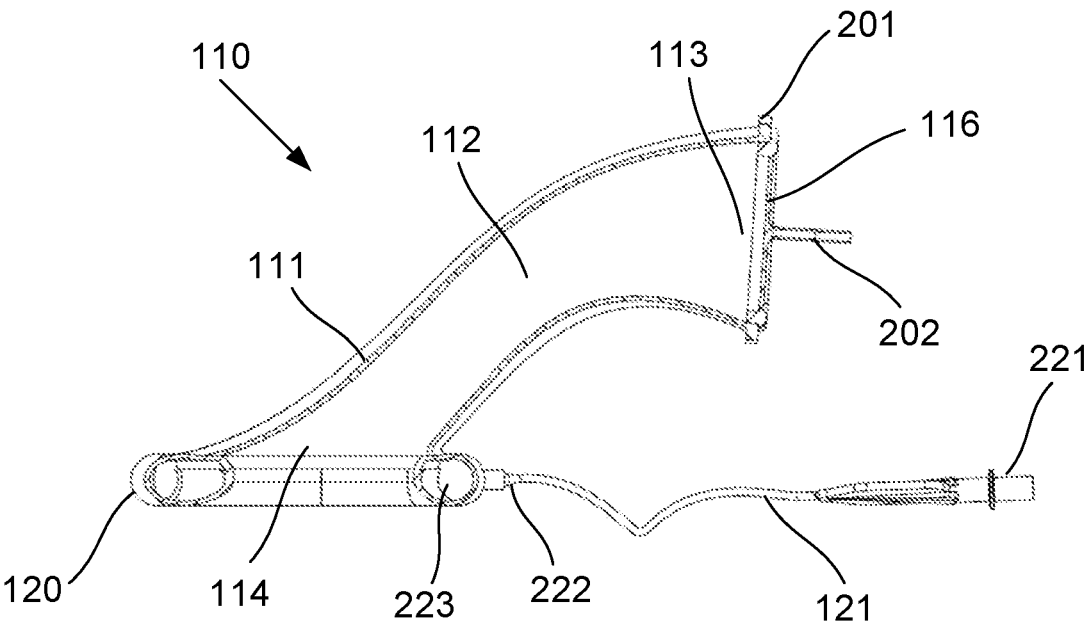
FIGS. 2C and 2D are cross section views of the LMA intubation guide of FIGS. 2A and 2B.
Figure 2D:
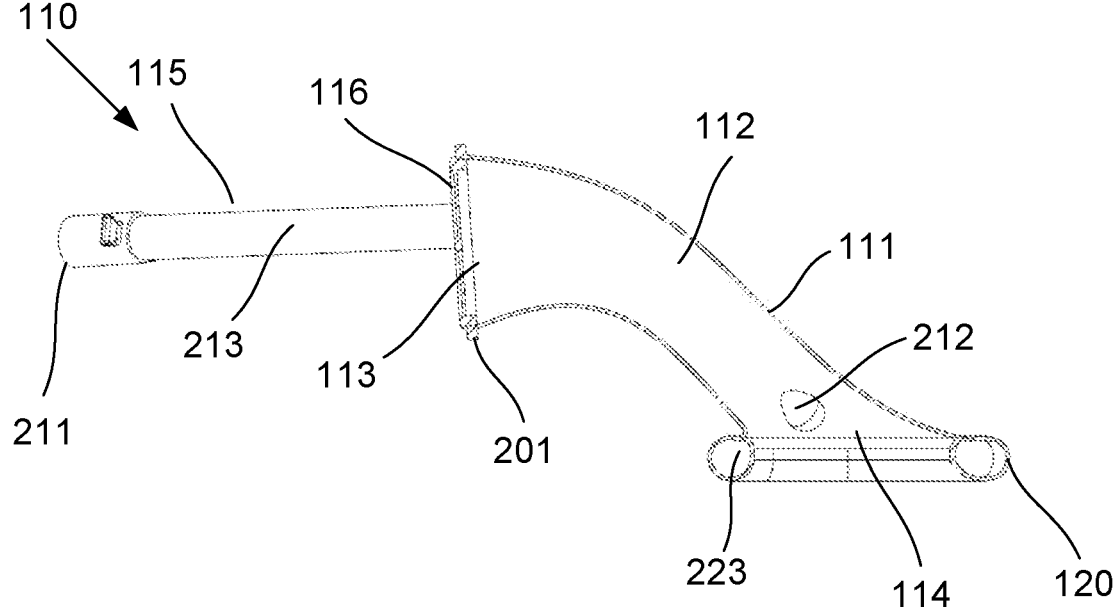
Figures 2E, 2F:
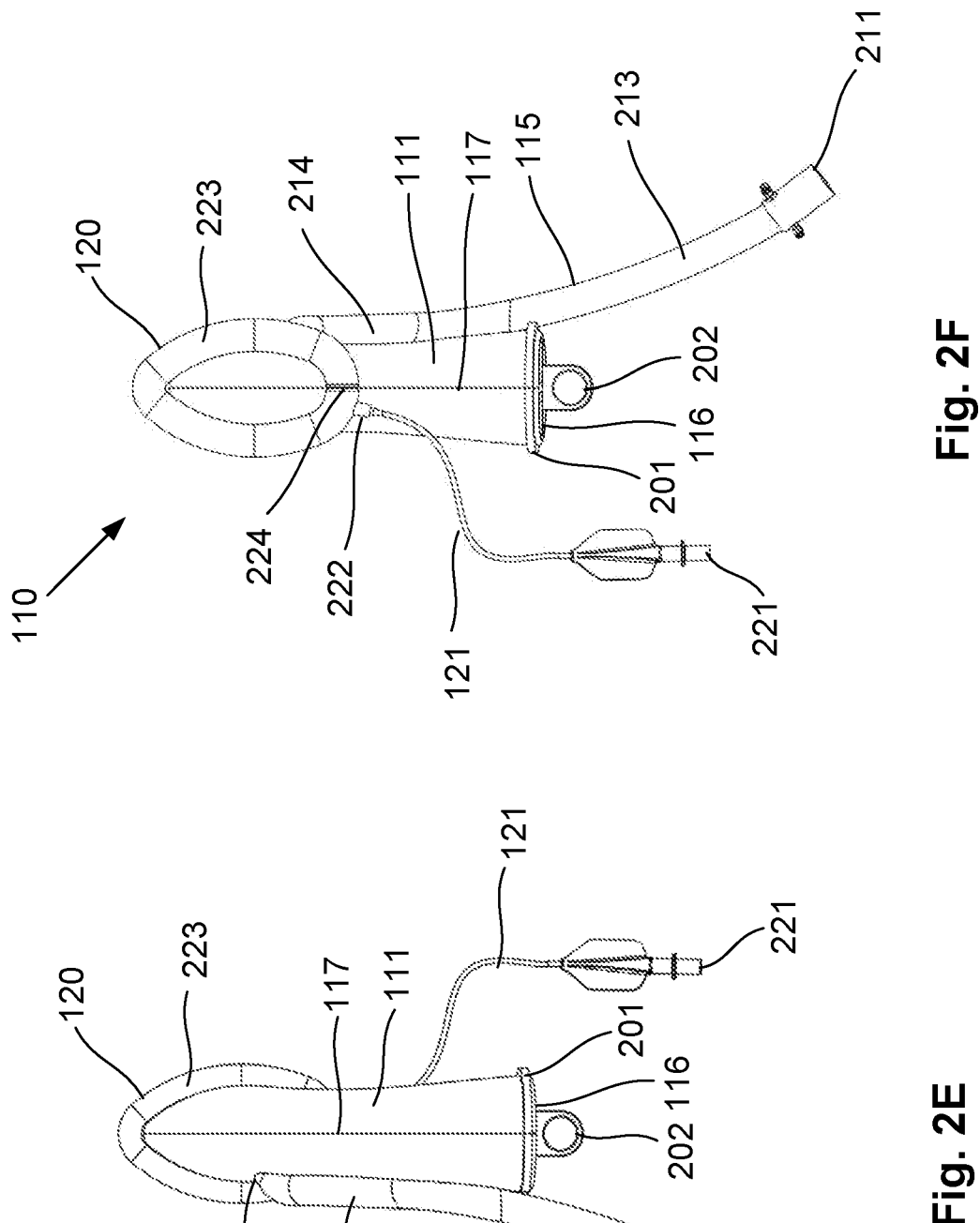
FIGS. 2E and 2F are respective top and bottom views of the LMA intubation guide of FIGS. 2A and 2B.

With regard to the detailed example of the LMA intubation guide 110 shown in FIGS. 2C and 2D, it can be seen that the elongate body 111 may be defined as a thin walled body to define the passageway 112. The body 111 will typically be formed from a rigid, semi-rigid or flexible material such as a suitable medical grade plastic material. Transparency may be a desirable quality as mentioned above, but is not essential.

In some alternative examples, the LMA intubation guide 110 may include a flange (not shown) surrounding the proximal opening 113. The flange may be configured to assist in correct insertion of the LMA intubation guide 110 by abutting the subject's mouth 102, to thereby ensure that the proximal opening 113 remains positioned outside the mouth. However, if such a flange is provided, it should not prevent full insertion of the LMA intubation guide 110 such that the laryngeal mask 120 is correctly positioned to provide a seal over the larynx 104 of the subject 100.

As mentioned above, it may be desirable to provide an LMA intubation guide 110 that is configured to be broken along the passageway 112 and the laryngeal mask 120, to facilitate removal of the LMA intubation guide 110 while the endotracheal tube 150 remains in place.

In this particular example, the body 111 of the LMA intubation guide 110 includes a break line 117 extending longitudinally along a side of the passageway 112, to thereby allow the LMA intubation guide 110 to be broken along the break line 117.

The break line 117 could be formed by providing a region of significantly thinner material compared to the material making the walls of the body 111, such that this thinner region would be breakable when opposing sides of the body 111 are forcibly pulled apart. A hinge line may be defined on the opposite side of the passageway 112 so that the intubation guide 110 can be broken into two hingedly connected portions, to aid in removal while the endotracheal tube 150 remains in place.

In this case, it will be seen that the break line 117 is defined along a central plane of the intubation guide 110. This break line 117 will be aligned with a sagittal plane of the subject in use. However, it should be appreciated that the particular configuration of the break lines 117 in the depicted configuration is not essential, and the LMA intubation guide 110 may include a different arrangement to allow it to be broken to facilitate its removal.

As mentioned above, the break line 117 may extend through the mask cuff 223, in the form of a partition 224 in the mask cuff 223, which can be seen in use in FIGS. 5A and 5B. Thus, when the body 111 of the LMA intubation guide 110 is broken apart to allow removal of the LMA intubation guide 110 whilst leaving the endotracheal tube 150 in place, the mask cuff 223 of the laryngeal mask 120 will open at the partition 224.

The proximal opening 113 and the passageway 112 of the LMA intubation guide 110 will typically have cross sections that are selected to receive the blade portion 142 of the intubation device 140. It will thus be appreciated that the particular cross section shape will depend on the design of the intubation device 140. The proximal opening 113 and the passageway 112 will accommodate the cross section shape of the blade portion 142 as shown in FIG. 4B. However the shape may vary depending on the particular shape of the blade portion 142 at different points along its length.

Accordingly, a shape of the proximal opening 113 and the passageway 112 may be selected based on a cross section shape of the blade portion 142 of the intubation device 140. As mentioned above, the LMA intubation guide 110 may be curved, and if so, the curvature of the LMA intubation guide 110 may be selected based on a curvature of the blade portion 142 of the intubation device 140.

The degree of curvature may also depend on a range of other factors including the flexibility of the material used to form the body 111 and the airway anatomy of the subject. For instance, as discussed above, the use of a more flexible material may allow a straight or relatively uncurved body 111 to deform in use and conform to the blade portion 142 and/or the subject's airway. It should be appreciated that the curvature of the body 111 may be less critical if it is formed from a relatively flexible material. It should be noted, however, that there will be a practical limit to the flexibility of the LMA intubation guide 110 to prevent its collapse upon insertion into the subject's mouth.

Furthermore, the use of a relatively more flexible material to form the body 111 of the intubation guide 110 may allow different sizes and shapes of the blade portion 142 to be accommodated, whereas the use of a relatively more rigid material may limit the range of blade types such that different LMA intubation guides 110 may need to be selected for different sizes and shapes of the blade portion 142.

It should be noted that a variety of different shapes and sizes of LMA intubation guides 110 may be provided to accommodate the range of different types, shapes and sizes of blades that may be used with the intubation device to suit patients having different ages, sizes and anatomical configurations. For instance, different LMA intubation guides 110 may be provided for use with pediatric, adult or obese subjects, and will be selected to correspond with the selected blade for the particular subject.

However, some of the above described techniques, such as the use of flexible materials to form the LMA intubation guide 110 may allow the same LMA intubation guide 110 to be used with a range of different blades.

The size of the proximal opening 113 and the passageway 112 may be selected based on the cross section size of the blade portion 142 of the intubation device 140. In some examples, the proximal opening 113 of the LMA intubation guide 110 may be deliberately constructed so that its size is smaller than a corresponding cross section size of the blade portion 142 of the intubation device 140. Similarly, the passageway 112 of the LMA intubation guide 110 may be deliberately constructed so that its size is smaller than a corresponding cross section size of the blade portion 142 of the intubation device 140. Providing a smaller sized proximal opening 113 and/or passageway 112 can ensure a snug fit which can help to seal against the escape of gases around the blade portion 142 at its interfaces with the proximal opening 113 and passageway 112.

This sealing effect may be more pronounced if a flexible material is used to form the LMA intubation guide 110, since this may enable the proximal opening and/or passageway 112 to be sized significantly smaller than the corresponding cross section size of the blade portion 142 and stretch to accommodate the blade portion 142 in use. In this regard, it will be appreciated that the LMA intubation guide 110 may be configured to expand when receiving the blade portion 142. Forming the LMA intubation guide 110 from an expandable material can thus allow the blade portion 142 to be more tightly enclosed within the LMA intubation guide 110 in use.

In some embodiments, the LMA intubation guide may additionally include a gastric tube conduit, thereby enabling the option of additionally advancing a gastric tube into the oesophagus of the subject via the gastric tube conduit, using a method as illustrated in FIGS. 6A to 6F.

Figure 6A:
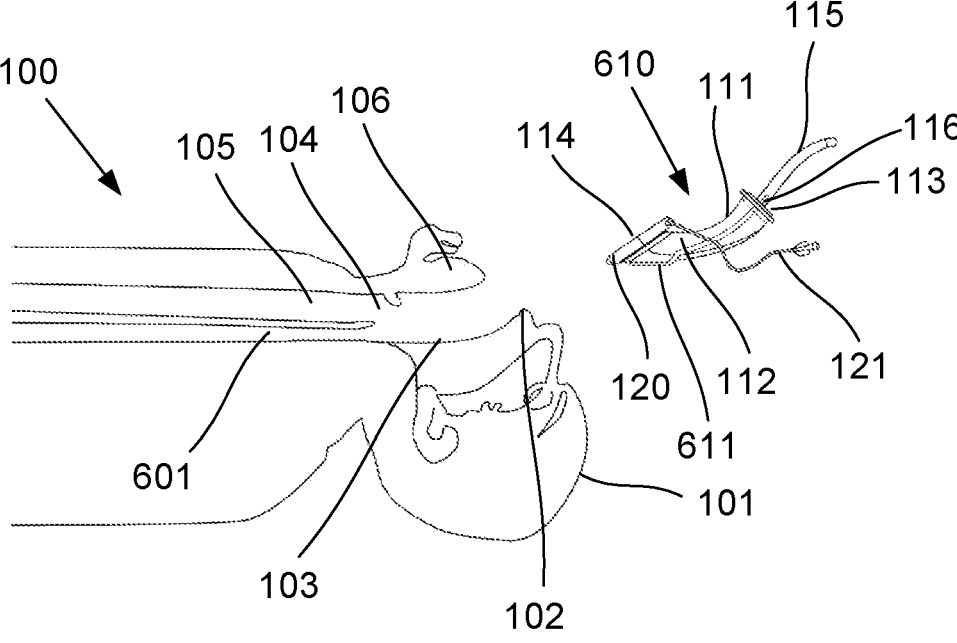
FIGS. 6A to 6F are cross section views showing steps of insertion of a gastric tube into an oesophagus of a subject using a second example of an LMA intubation guide having a gastric tube conduit.

With reference to FIG. 6A, the method commences in a similar manner as the above described ventilated endotracheal intubation method using the LMA intubation guide 110, with the subject 100 lying in a supine position. Once again, the subject's head 101 may be tilted, to adjust the relative positioning of the subject's mouth 102, pharynx 103 and larynx 104 to better facilitate access to the larynx during the procedure.

At FIG. 6A, the LMA intubation guide 610 is provided for insertion into the mouth 102 of the subject 100, but in this case the LMA intubation guide 610 further includes a gastric tube conduit 611. Further details of this example of the LMA intubation guide 110 can be seen in FIGS. 7A and 7B.

Aside from the additional inclusion of the gastric tube conduit 611, this version of the LMA intubation guide 610 may have a substantially the same configuration as the previously described version of the LMA intubation guide 110. Thus, the LMA intubation guide 610 will generally include an elongate body 111 defining a passageway 112 extending between a proximal opening 113 and a distal opening 114, a laryngeal mask 120 positioned at the distal opening 114, and a ventilation airway 115 extending at least partially along the body 111.

Figure 6B:
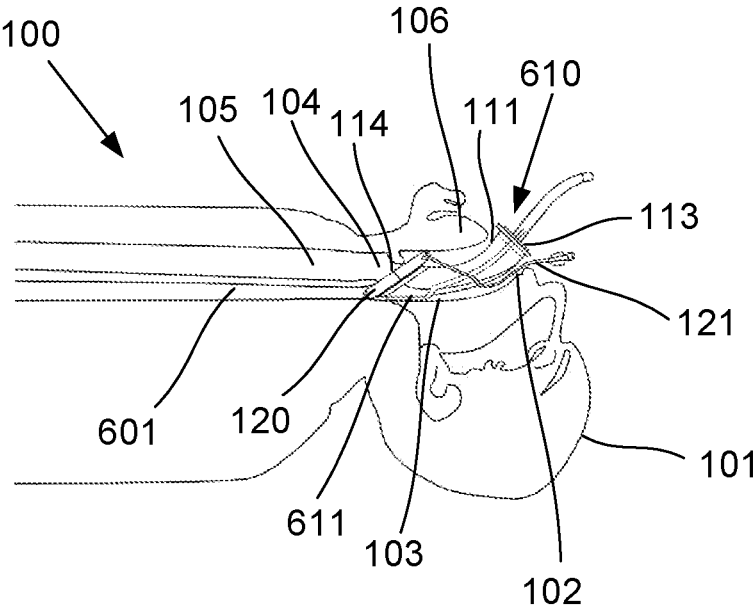

As per the previous ventilated intubation method, the LMA intubation guide 610 is inserted into the mouth 102 of the subject 100 as shown in FIG. 6B. When the LMA intubation guide 610 has been properly inserted, the laryngeal mask 120 will be positioned proximate to a larynx 104 of the subject 100 and the proximal opening 113 will be positioned proximate to the mouth 102 of the subject 100. The larynx 104 of the subject 100 will be covered with the laryngeal mask 120. If an inflatable mask cuff 223 is provided this can be inflated to form a seal around the larynx 104.

Figure 6C:
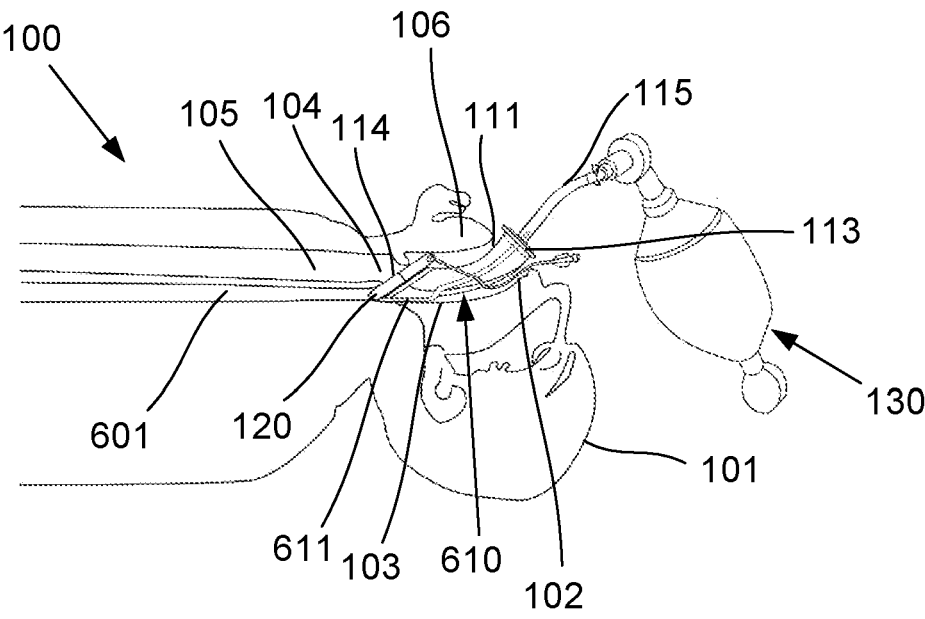

With regard to FIG. 6C, once the LMA intubation guide 610 has been inserted so that the subject's larynx 104 is covered by the laryngeal mask 120, the subject 100 may be ventilated using the ventilation airway 115 of the LMA intubation guide 610. As discussed above, this may involve connecting a ventilator 130 to the ventilation airway 115 so that a ventilation gas can be supplied via the ventilation airway to a delivery point proximate to the laryngeal mask 120.

Ventilation of the subject 100 can continue to be performed as shown in FIG. 6C as required, and in this regard it will be appreciated that the LMA intubation guide 610 may be used in a similar manner as a traditional laryngeal mask airway device.

Figure 6D:
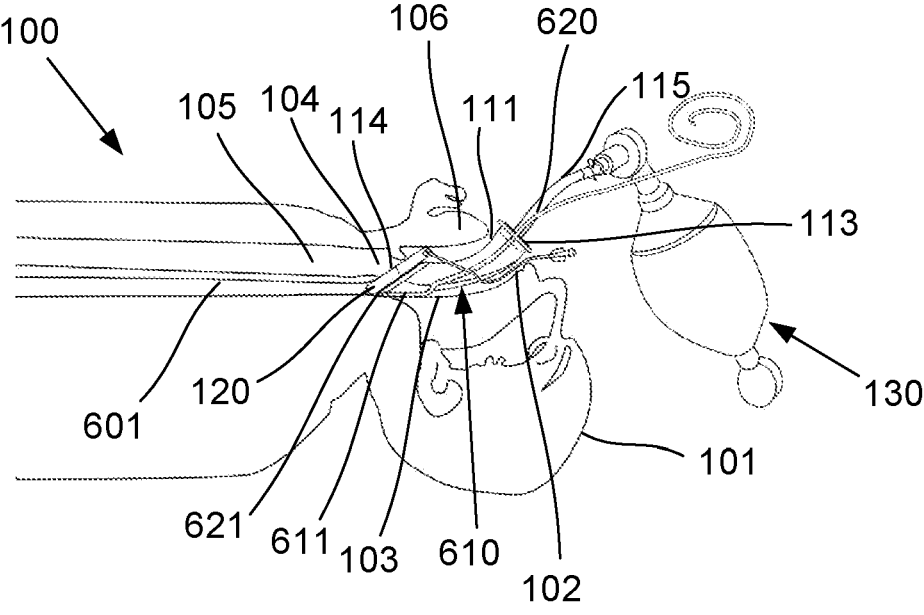

Turning to FIG. 6D, while the subject 100 is being ventilated, a gastric tube 620 may be fed through the gastric tube conduit 611.

Figure 7A:
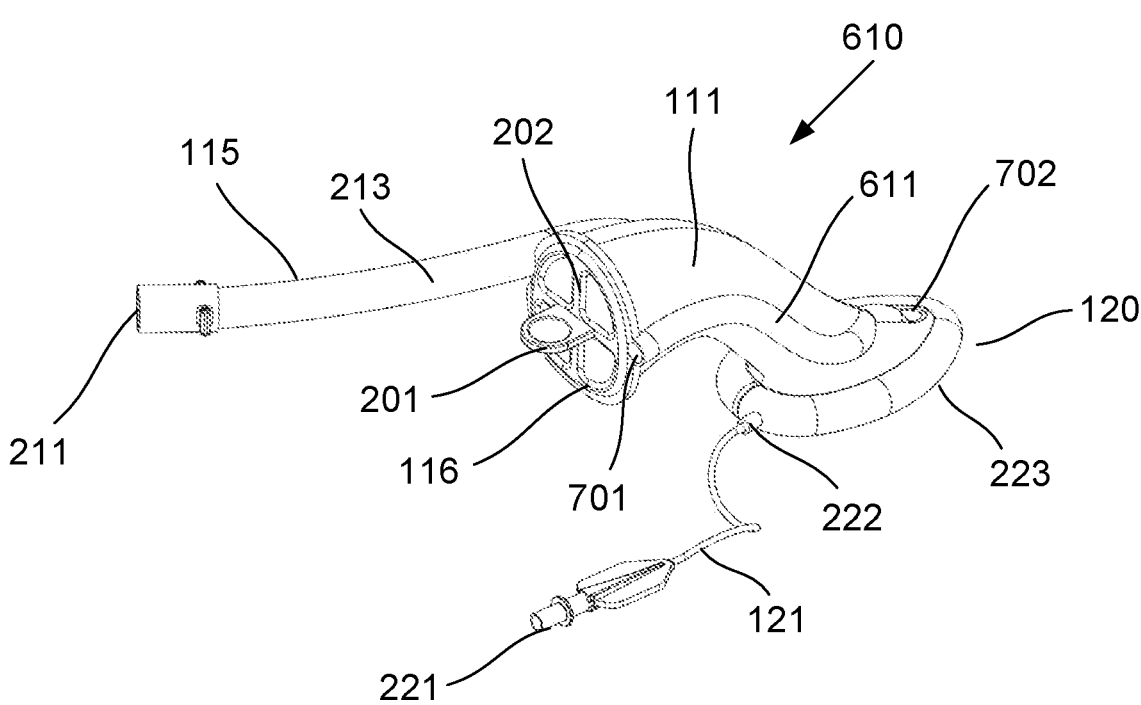
FIGS. 7A and 7B are perspective views of the second example of the LMA intubation guide of FIGS. 6A to 6F.
Figure 7B:
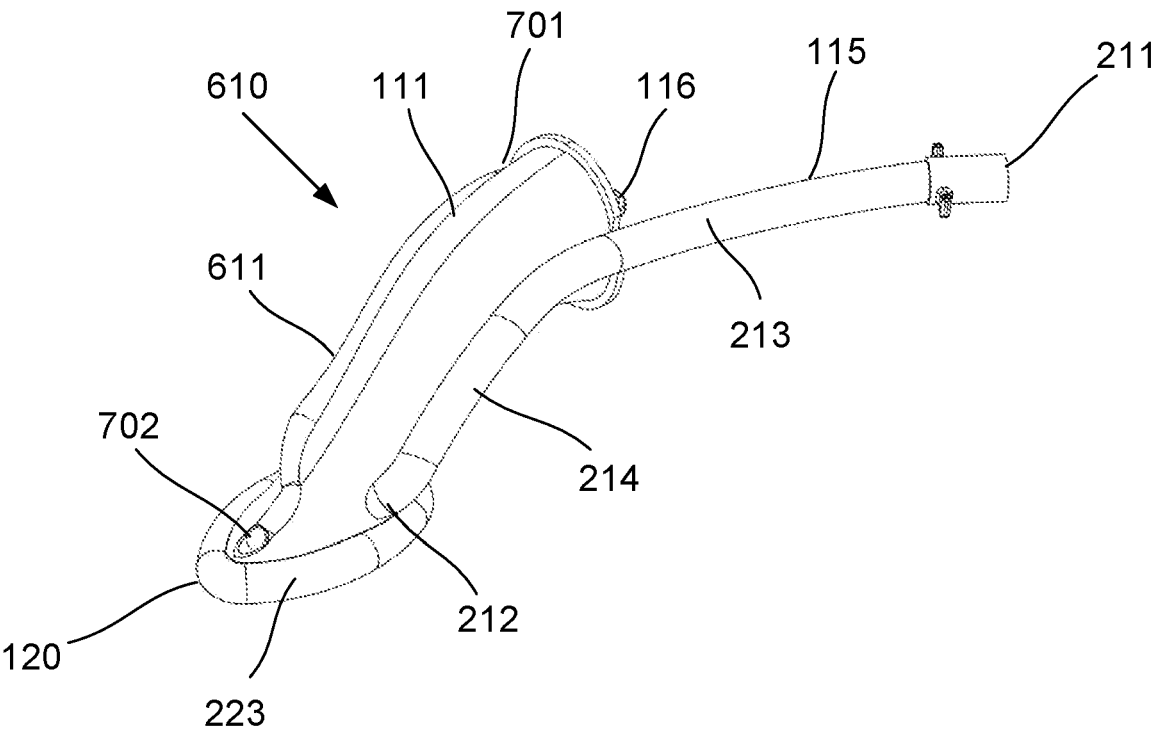

With regard to FIGS. 7A and 7B, it will be seen that the gastric tube conduit 611 may extend along the body 111 and include a gastric tube conduit port 701 at a proximal end of the gastric tube conduit 611 and a gastric tube aperture 702 at a distal end of the gastric tube conduit. The gastric tube aperture 702 is typically configured for allowing the gastric tube to be advanced from the gastric tube aperture 702 into the oesophagus. In this example, the gastric tube aperture

702 is positioned outside of the laryngeal mask 120 and the passageway 112, but this positioning will depend on the design of the laryngeal mask and location of the gastric tube aperture 702 relative to the oesophagus 601. The gastric tube aperture 702 will preferably positioned near the most distal end of the laryngeal mask 120 so as place the gastric tube as close to the oesophagus as possible.

Figure 6E:
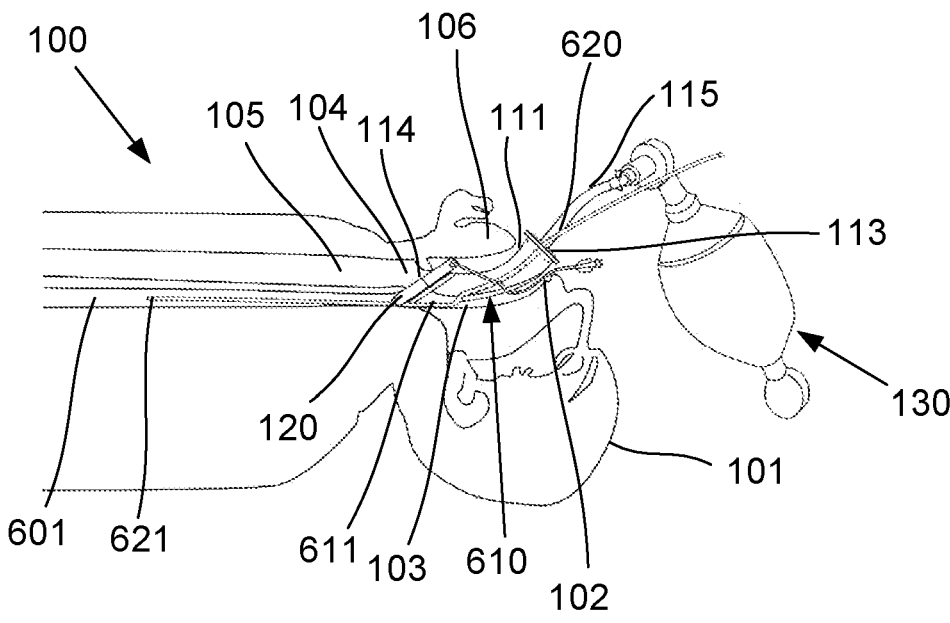

A gastric tube tip 621 of the gastric tube 620 may then be advanced from the gastric tube conduit 611, via the gastric tube aperture 702, and into the oesophagus 601 of the subject 100, as shown in FIG. 6E. The gastric tube aperture 702 will preferably configured to face towards the oesophagus 601 of the subject in use to thereby assist in directing the gastric tube tip 621 towards the oesophagus 601.

Figure 6F:
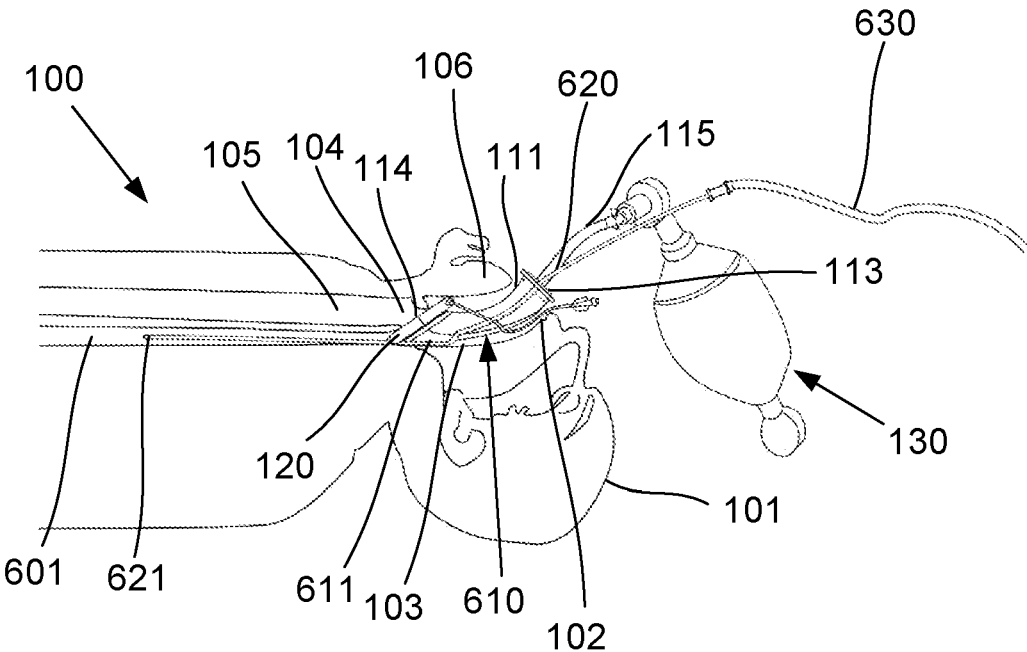

Finally, as shown in FIG. 6F, the gastric tube 620 may then be connected to tubing 630 which may in turn be connected to a suction source or other medical equipment for utilising the gastric tube as required.

Following the sequence of steps shown in FIGS. 6A to 6F, it will be appreciated that the endotracheal intubation method as describe above can subsequently be performed essentially as shown and described in FIGS. 1D to 1J.

It should be appreciated that the LMA intubation guide 610 may be configured to allow the gastric tube 620 to be inserted independently of intubation of the subject being performed. Furthermore, it should be appreciated that the LMA intubation guide 610 may be configured to still allow the ventilation of the subject independently of intubation of the subject being performed. Thus, the gastric tube conduit 611 will preferably be provided separately from the passageway 112 to allow insertion of the gastric tube 620 without interfering with other ventilation and endotracheal intubation functionalities of the LMA intubation guide 610 as described above.

Turning again to FIGS. 7A and 7B, it will be seen that the gastric tube conduit 611 may be offset from the passageway 112 in a similar manner as per the ventilation airway 115. The gastric tube conduit 611 may also be offset laterally relative to a central plane of the LMA intubation guide 110. In some examples, the ventilation airway 115 and the gastric tube conduit 611 may be offset from the passageway 112 on opposing sides of the passageway 112. Furthermore, the gastric tube conduit 611 may be integrally formed with the body 111 of the LMA intubation guide, in a similar manner as per the airway body portion 214 of the ventilation airway 115 that extends along the body 111. However, this positioning is not essential and different embodiments may have different gastric tube conduit 611 locations relative to other features of the LMA intubation guide 110.

Figure 10A:
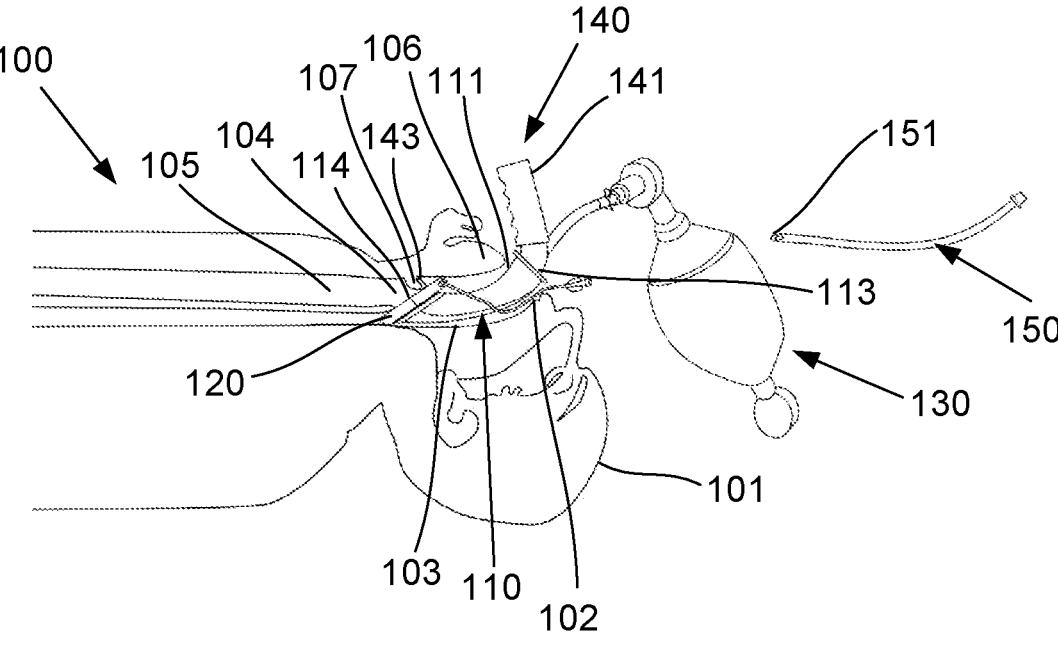
FIGS. 10A and 10B are cross section views showing steps of manually advancing an endotracheal tube using a conventional laryngoscope with the first example of the LMA intubation guide.
Figure 10B:
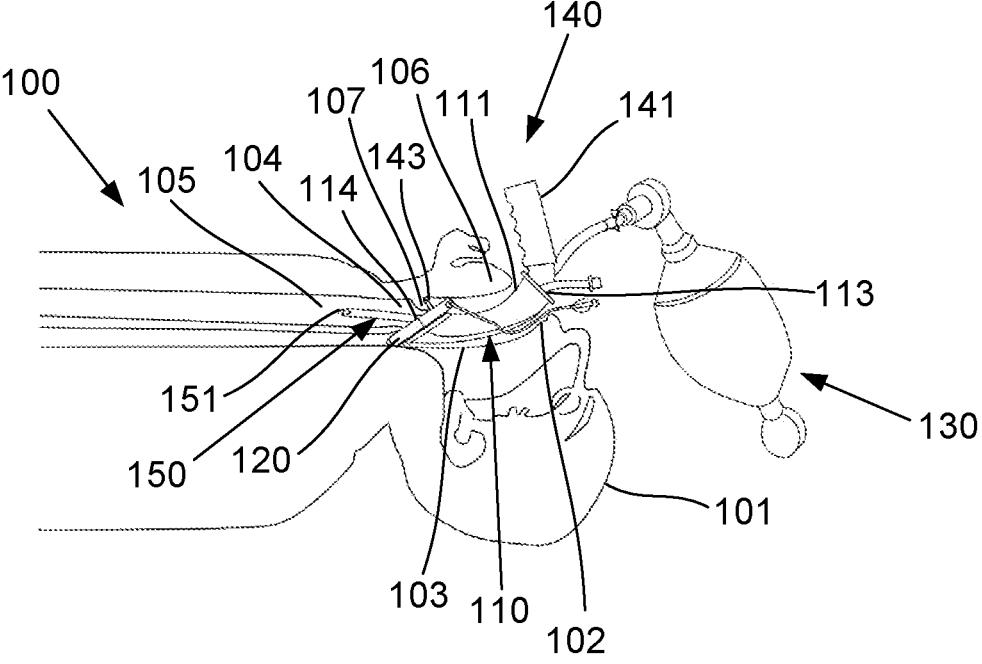

FIGS. 10A and 10B are cross section views showing steps of manually advancing an endotracheal tube using a conventional laryngoscope with the first example of the LMA intubation guide 110. It should be appreciated that the steps depicted in FIGS. 10A and 10B effectively replace the steps depicted in FIGS. 1E and 1F of the method described with reference to FIGS. 1A to 1J, but using a conventional laryngoscope as the intubation device 140 instead of the single handed version of the intubation device shown previously. It will be appreciated that the conventional laryngoscope in this example may be either a direct vision or video laryngoscope.

It is assumed that the blade portion 142 of the intubation device 140 is inserted into the passageway 112 of the LMA intubation guide 110 generally as described above with regard to FIG. 1E. But, with regard to FIG. 10A, in this case the endotracheal tube 150 is provided separately from the intubation device 140. Turning to FIG. 10B, the endotracheal tube 150 is manually advanced along the blade portion 142 of the intubation device 140 and through the passageway 112, to introduce the tip 151 of the endotracheal tube 150 into the trachea 105 of the subject. Then the rest of the method can continue generally as previously described above with reference to FIGS. 1G to 1J.

It will be understood that, when a conventional laryngoscope is used as the intubation device 140 in this manner, the user will typically use one hand to hold the handle 141 of the intubation device 140 and another hand to manually advance the endotracheal tube 150.

In any event, it will be appreciated that the above described methods and different embodiments of the LMA intubation guide can allow endotracheal intubation to be performed, with ventilation being provided throughout the procedure via a laryngeal mask airway to reduce the risks associated with loss of ventilation during the procedure, whilst using a familiar intubation device.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means ±20%.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

The invention claimed is:

1. A laryngeal mask airway (LMA) intubation guide for use in an endotracheal intubation procedure and in ventilation of a subject, the LMA intubation guide including:
   a) an elongate body defining a passageway extending between a proximal opening and a distal opening, the passageway being configured for receiving a blade portion of an intubation device;
   b) a laryngeal mask at the distal opening, the laryngeal mask being for covering the larynx of the subject; and
   c) a ventilation airway extending at least partially along the body, the ventilation airway including:
   i) a ventilation port at a proximal end of the ventilation airway for connection to a ventilator; and
   ii) a ventilation aperture at a distal end of the ventilation airway for allowing fluid communication between the ventilation airway and the passageway proximate to the laryngeal mask,
   wherein the LMA intubation guide is configured for insertion into a mouth of the subject so that the proximal opening is positioned proximate to the mouth of the subject and the laryngeal mask is positioned proximate to a larynx of the subject, to thereby allow the blade portion of the intubation device to be inserted into the passageway of the LMA intubation guide to allow intubation of the subject using an endotracheal tube through the passageway, while the subject is ventilated using the ventilation airway;

wherein the LMA intubation guide includes a seal covering the proximal opening, the seal normally being in a closed position for sealing the proximal opening and being moveable to an open position when the blade portion of the intubation device is inserted through the passageway;
   wherein the seal includes at least one resilient membrane configured to deform in response to the blade portion being urged against the seal, to thereby define an opening for receiving the blade portion;
   wherein the at least one resilient membrane is supported around a perimeter of the proximal opening, the at least one resilient membrane including an aperture that is substantially closed in the closed position and that stretches to define the opening in the open position;
   wherein the at least one resilient membrane comprises:
      two or more resilient membranes that are supported around the perimeter of the proximal opening, the respective aperture of each one of the resilient membranes differing from the apertures of other ones of the resilient membranes in at least one of: shape; location; and orientation; or
      the at least one resilient membrane comprises two or more resilient membranes that are each supported around a respective part of a perimeter of the proximal opening and that each include a respective unsupported edge, the unsupported edges at least partially overlapping in the closed position and separating to define the opening in the open position.

2. An LMA intubation guide according to claim 1, wherein the laryngeal mask includes a mask cuff for forming a seal around the larynx of the subject.

3. An LMA intubation guide according to claim 1, wherein the ventilation aperture is located inside the passageway, proximate to the laryngeal mask.

4. An LMA intubation guide according to claim 3, wherein the ventilation aperture is configured to direct a flow of ventilation gas towards the larynx of the subject.

5. An LMA intubation guide according to claim 1, wherein the ventilation airway is offset from the passageway.

6. An LMA intubation guide according to claim 1, wherein the ventilation airway includes an airway body portion that extends along the body.

7. An LMA intubation guide according to claim 1, wherein at least the airway body portion is formed integrally with the body.

8. An LMA intubation guide according to claim 7, wherein the ventilation airway includes an airway conduit portion that extends away from the proximal opening.

9. An LMA intubation guide according to claim 1, wherein the LMA intubation guide includes a closure for covering the proximal opening when the blade portion is not inserted through the passageway.

10. An LMA intubation guide according to claim 1, wherein the seal is biased towards the closed position, such that the seal returns towards the closed position when the blade portion of the intubation device is removed from the passageway.

11. An LMA intubation guide according to claim 10, wherein the seal is configured to form a partial seal surrounding at least one of the blade portion of the intubation device and the endotracheal tube in use.

12. An LMA intubation guide according to claim 1, wherein the LMA intubation guide includes a removable cap for closing the proximal opening when the blade portion of the intubation device is not being inserted into the passageway of the LMA intubation guide.

13. An LMA intubation guide according to claim 12, wherein the cap includes a seal for covering the proximal opening, the seal normally being in a closed position for sealing the proximal opening and being moveable to an open position when the blade portion of the intubation device is inserted through the passageway.

14. An LMA intubation guide according to claim 1, wherein the LMA intubation guide includes a flange surrounding the proximal opening.

15. An LMA intubation guide according to claim 14, wherein the flange is configured to prevent over-insertion of the LMA intubation guide by abutting the subject's mouth to thereby ensure that the proximal opening remains positioned outside the mouth.

16. An LMA intubation guide according to claim 1, wherein the LMA intubation guide is configured to be broken along the passageway and the laryngeal mask.

17. An LMA intubation guide according to claim 16, wherein the body of the LMA intubation guide includes a break line extending longitudinally along a side of the passageway and the laryngeal mask, to thereby allow the LMA intubation guide to be broken along the break line.

18. An LMA intubation guide according to claim 1, wherein a shape of the proximal opening is selected based on a cross section shape of the blade portion of the intubation device; a size of the proximal opening is selected based on a cross section size of the blade portion of the intubation device; or both.

19. An LMA intubation guide according to claim 1, wherein a shape of the passageway is selected based on a cross section shape of the blade portion of the intubation device; a size of the passageway is selected based on a cross section size of the blade portion of the intubation device; or both.

20. An LMA intubation guide according to claim 1, wherein the LMA intubation guide is formed from a flexible material.

21. An LMA intubation guide according to claim 20, wherein the LMA intubation guide is configured to expand when receiving the blade portion.

22. An LMA intubation guide according to claim 1, wherein the LMA intubation guide is curved, and wherein a curvature of the LMA intubation guide is selected based on a curvature of the blade portion of the intubation device.

23. An LMA intubation guide according to claim 1, wherein the LMA intubation guide includes a gastric tube conduit for allowing a gastric tube to be advanced into the oesophagus of the subject via the gastric tube conduit.

24. An LMA intubation guide according to claim 23, wherein the gastric tube conduit extends along the body and includes a gastric tube conduit port at a proximal end of the gastric tube conduit and a gastric tube aperture at a distal end of the gastric tube conduit for allowing the gastric tube to be advanced from the gastric tube aperture into the oesophagus.

25. An LMA intubation guide according to claim 24, wherein at least one of:
   a) the gastric tube aperture is positioned outside of the laryngeal mask and the passageway;
   b) the gastric tube aperture is configured to face towards an oesophagus of the subject in use;
   c) the gastric tube conduit is offset from the passageway;
   d) the ventilation airway and the gastric tube conduit are offset from the passageway on opposing sides of the passageway; and e) the LMA intubation guide is configured to allow the gastric tube to be inserted independently of intubation of the subject being performed.

26. An LMA intubation guide according to claim 1, wherein the LMA intubation guide is configured to allow ventilation of the subject independently of intubation of the subject being performed.

27. A method for use in an endotracheal intubation procedure, the method including:
   a) inserting a laryngeal mask airway (LMA) intubation guide into a mouth of a subject, the LMA intubation guide including:
   i) an elongate body defining a passageway extending between a proximal opening and a distal opening, the passageway being configured for receiving a blade portion of an intubation device, the proximal opening being positioned proximate to a mouth of the subject;
   ii) a laryngeal mask positioned at the distal opening and being positioned proximate to a larynx of the subject; and
   iii) a ventilation airway extending at least partially along the body, the ventilation airway including:
     (1) a ventilation port at a proximal end of the ventilation airway for connection to a ventilator; and
     (2) a ventilation aperture at a distal end of the ventilation airway for allowing fluid communication between the ventilation airway and the passageway proximate to the laryngeal mask;
   b) covering the larynx of the subject with the laryngeal mask;
   c) connecting a ventilator to the ventilation port and ventilating the subject using the ventilation airway; and
   d) while ventilation of the subject continues:
     i) inserting the blade portion of the intubation device into the passageway of the LMA intubation guide;
     ii) positioning a distal end of the blade portion of the intubation device proximate to the larynx of the subject; and
     iii) advancing an endotracheal tube along the blade portion of the intubation device through the passageway into a trachea of the subject;
   wherein the LMA intubation guide includes a seal covering the proximal opening, the seal normally being in a closed position for sealing the proximal opening and being moveable to an open position when the blade portion of the intubation device is inserted through the passageway,
   wherein the seal includes at least one resilient membrane configured to deform in response to the blade portion being urged against the seal, to thereby define an opening for receiving the blade portion,
   wherein the at least one resilient membrane is supported around a perimeter of the proximal opening, the at least one resilient membrane including an aperture that is substantially closed in the closed position and that stretches to define the opening in the open position;
   wherein the at least one resilient membrane comprises:
     two or more resilient membranes that are supported around the perimeter of the proximal opening, the respective aperture of each one of the resilient membranes differing from the apertures of other ones of the resilient membranes in at least one of: shape; location; and orientation; or
     the at least one resilient membrane comprises two or more resilient membranes that are each supported around a respective part of a perimeter of the proximal opening and that each include a respective unsupported edge, the unsupported edges at least partially overlapping in the closed position and separating to define the opening in the open position.

\* \* \* \* \*